United States Patent [19]

Wilson

[11] Patent Number: 5,489,527
[45] Date of Patent: Feb. 6, 1996

[54] TRANSLATION OF M-RNA

[75] Inventor: Thomas M. A. Wilson, Norwich, England

[73] Assignee: Diatech Limited, London, United Kingdom

[21] Appl. No.: 46,358

[22] Filed: Apr. 12, 1993

Related U.S. Application Data

[63] Continuation of Ser. No. 148,650, filed as PCT/6B87/00390, Jun. 4, 1987, abandoned.

[30] Foreign Application Priority Data

Jun. 4, 1986 [GB] United Kingdom .................. 8613481

[51] Int. Cl.$^6$ .............................. C12N 5/10; C12N 1/21; C12N 15/67; C12N 15/11
[52] U.S. Cl. .................................. 435/240.1; 435/252.3; 435/240.2; 435/240.4; 435/252.33; 435/320.1; 536/24.1; 935/34; 935/35; 935/44; 935/66
[58] Field of Search ........................ 536/24.1; 435/320.1, 435/252.33, 69.1, 240.1, 240.2, 240.4, 252.3, 172.3; 935/33, 34, 35, 44, 45, 66

[56] References Cited

U.S. PATENT DOCUMENTS

| | | | |
|---|---|---|---|
| 4,820,639 | 4/1989 | Gehrke | 435/69.52 X |
| 4,962,028 | 10/1990 | Bedbrook et al. | 435/172.3 |

FOREIGN PATENT DOCUMENTS

| | | | |
|---|---|---|---|
| 5437886 | 9/1986 | Australia | C12N 15/00 |
| 471175 | 10/1987 | Australia | C12N 15/00 |
| 0067553 | 12/1982 | European Pat. Off. | C12N 15/00 |
| 0194809 | 9/1986 | European Pat. Off. | C12N 15/00 |
| 8703619 | 6/1987 | WIPO | C12N 15/00 |

OTHER PUBLICATIONS

Parks, G. D. et al. 1986. *J. Virology* vol. 60 p. 376–384.
Wilson, T. M. A. 1986. "Expression of the Large 5' Proximal Cistron of Tobacoo Mosaic Virus by 70s Ribosomes During Cotranslational Disassembly in a Prokaryotic Cell–Free System." *Virology* vol. 152 pp. 277–279.
Sleat, D. E., et al, 1987. "Characterization of the 5'–leader Sequence of Tobacco Mosaic Virus RNA as a General Enhancer of Translation in vitro". *Gene* vol. 17 pp. 217–225.
Science, vol. 231, 14 Mar. 1986, R. French et al.: "Bacterial gene inserted in an engineered RNA virus: efficient expression in monocotyle–donous plant cells", pp. 1294–1297.
Chemical Abstracts, vol. 103, 1985 (Columbus, Ohio, US) L. Sue Loesche–Fries et al.: "Expression of alfalfa mosaic virus RNA 4 cDNA transcripts in vitro and in vivo", see Abstract No. 190686.
Proc. Natl. Acad. Sci., vol. 83, Mar. 1986, (US) W. O. Dawson et al.: "cDNA cloning of the complete genome of tobacco mosaic virus and production of infectious transcripts", pp. 1832–1836.
Nucleic Acids Research, vol. 15, No. 8, 24–Apr.–1987 D. R. Gallie et al.: "The 5'–leader sequence of tobacco mosaic virus RNA enhances the expression of foreign gene transcripts in vitro and in vivo", pp. 3257–3273.

Proc. Natl. Acad. Sci. (USA), vol. 79, Oct. 1982, P. Goelet et al.: "Nucleotide sequence of tobacco mosaic virus RNA", pp. 5818–5822.
Biological Abstracts, vol. 82, No. 5, 1986 (Philadelphia, PA, US) L. Gehrke: "Preparation of messenger RNA transcripts for secondary structure analysis using SP6 polymerase, guanylyltransferase and preparative gel electrophoresis" see abstract No. 40900.
Chemical Abstracts, vol. 88, 1978 (Columbus, Ohio, US) K. Richards et al.: "Nucleotide sequence at the 5' extremity of tobacco mosaic virus RNA. 1. The noncoding region (nucleotides 1–68)", see p. 212, abstract No. 165637t.
Nature, vol. 316, 15–Aug.–1985 T. Hunt: "False starts in translational control of gene expression"pp. 580–581.
Biochemistry, vol. 22, 1983, American Chemical Society; L. Gehrke et al.: "5'–conformation of capped alfalfa mosaic virus ribonucleic acid 4 may reflect its independence of the cap structure or of cap–binding protein for efficient translation", pp. 5157–5164.
Chemical Abstracts, vol. 89, 1978 (Columbus, Ohio, US) W. Zagorski: "Translation regulation of expression of the brome–mosaic–virus RNA genome in vitro", see p. 213, abstract no. 72850n.
Nature, vol. 313, 28–Feb.–1985 J. T. Odell et al.: "Identification of DNA sequences required for activity of the cauliflower mosaic virus 35S promoter", pp. 810–812.
The EMBO Journal, vol. 4, No. 8, 1985; M. W. Bevan et al.: "Expression of tobacco mosaic virus coat protein by a cauliflower mosaic virus promoter in plants transformed by Agrobacterium", pp. 1921–1926.
Loesch–Fries et al. Virology, vol. 146, pp. 177–187 (1985).
Gehrke, L, Gene Anal. Tech 3(3) pp. 45–52, (1986).
Richard et al, European J. Biochemistry, 84(2), pp. 513–519 (1978).
W. Zagorski, European Journal of Biochemistry, 86(2), pp. 465–472 (1978).
Darlix et al., Nucleic Acids Res., 10(17), pp. 5183–5196 (1982).
Filipowicz & Haenni, Proc. Nat. Acad. Sci. (USA), vol. 76(7), pp. 3111–3115, (1979).
A Dictionary of Genetic Engineering (S. G. Oliver & J. M. Ward), Cambridge University Press, 1985, p. 35.
Mundry 2, Vererbungsl, 97, 281 (1965).
Mandeles, Journal of Biological Chemistry, vol. 243 (13), pp. 3671–3674 (1968).
Konarska et al., Eur. J. Biochem., vol. 114, pp. 221–227 (1981).
Wilson et al., J. Gen. Virol., vol. 66, pp. 1201–1207 (1985).

*Primary Examiner*—Mary E. Mosher
*Attorney, Agent, or Firm*—Oblon, Spivak, McClelland, Maier & Neustadt

[57] ABSTRACT

It has been found that the 5' regions of RNA viruses act as enhancers of translation of mRNA. The omega prime ($\Omega'$) sequence of Tobacco Mosaic Virus, derivatives and portions thereof, and 5' leader sequences of other RNA viruses can be ligated upstream of an appropriate mRNA or used in the form of cDNA in an expression vector. The translational enhancers are effective in many different types of expression system, for example plant cells, bacteria, and animal cells, and also in in vitro translation.

5 Claims, 19 Drawing Sheets

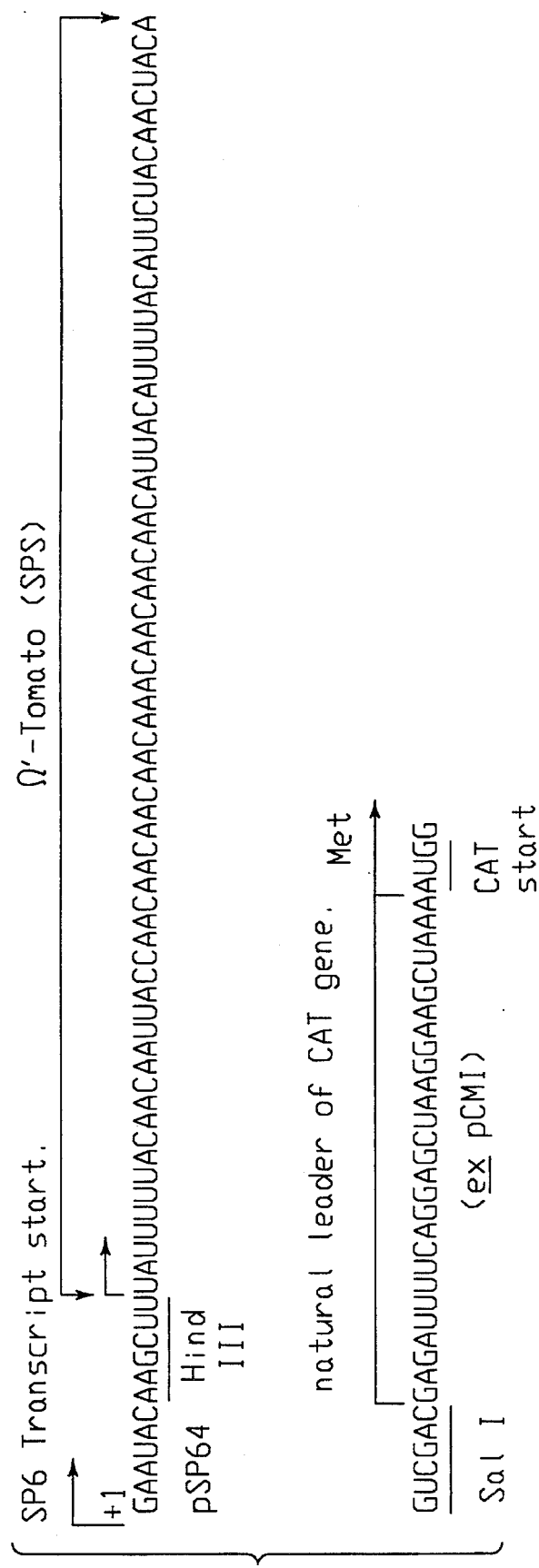
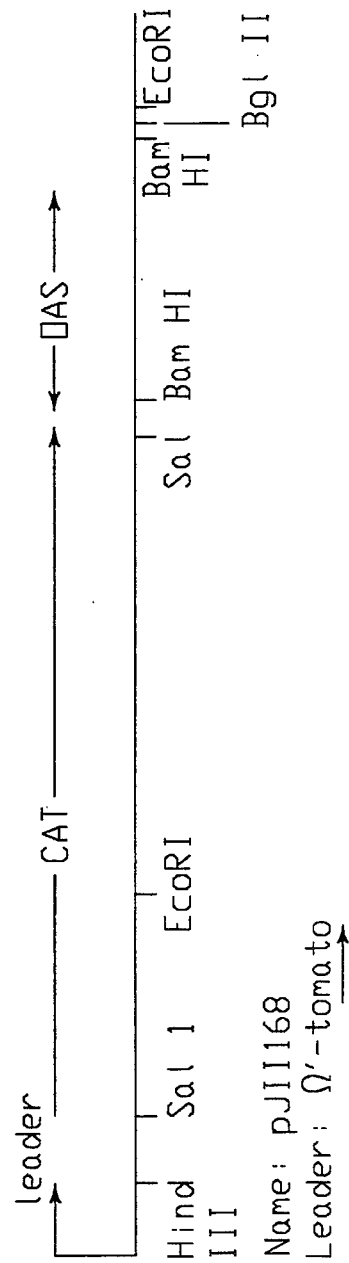
FIG. 5A
FIG. 5B

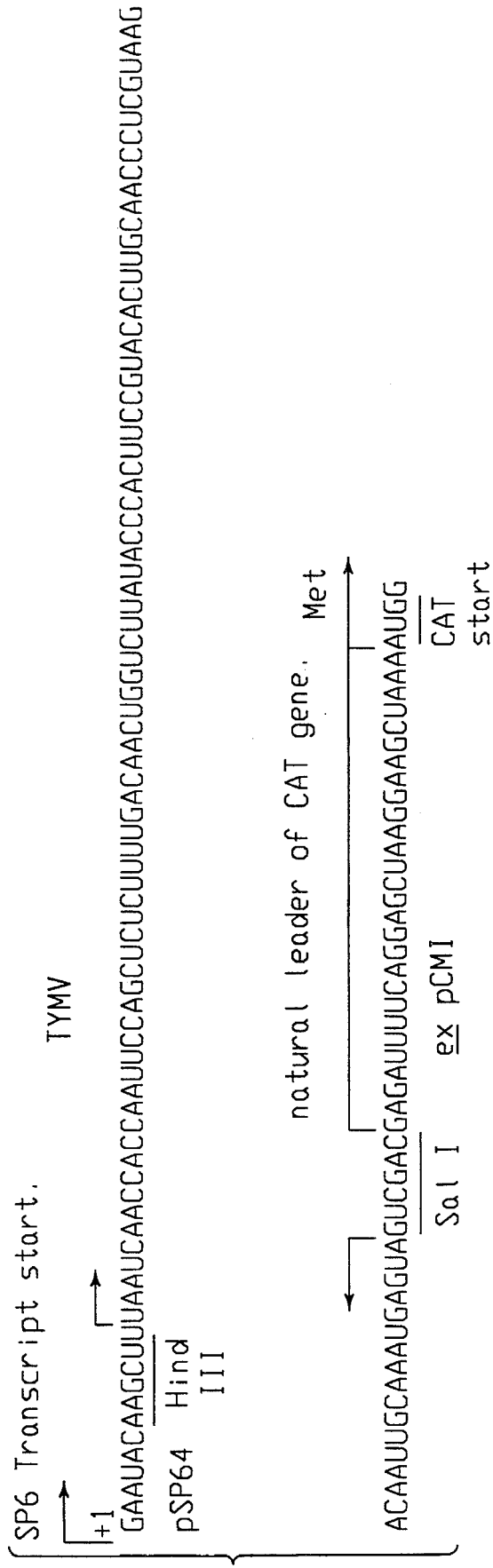
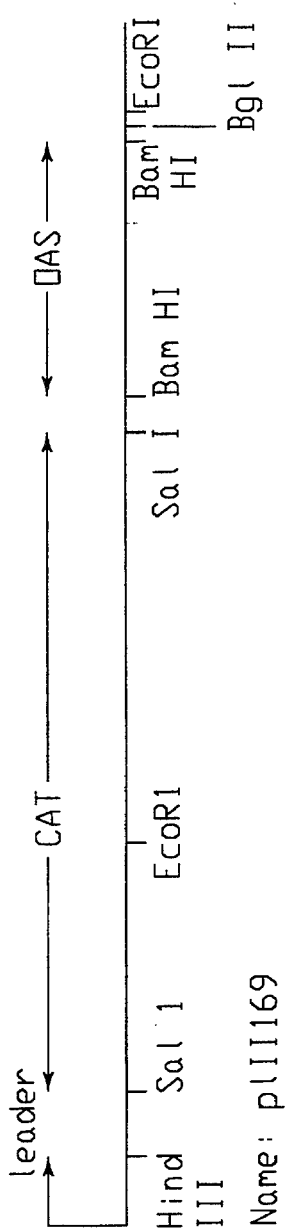
FIG. 6A
FIG. 6B

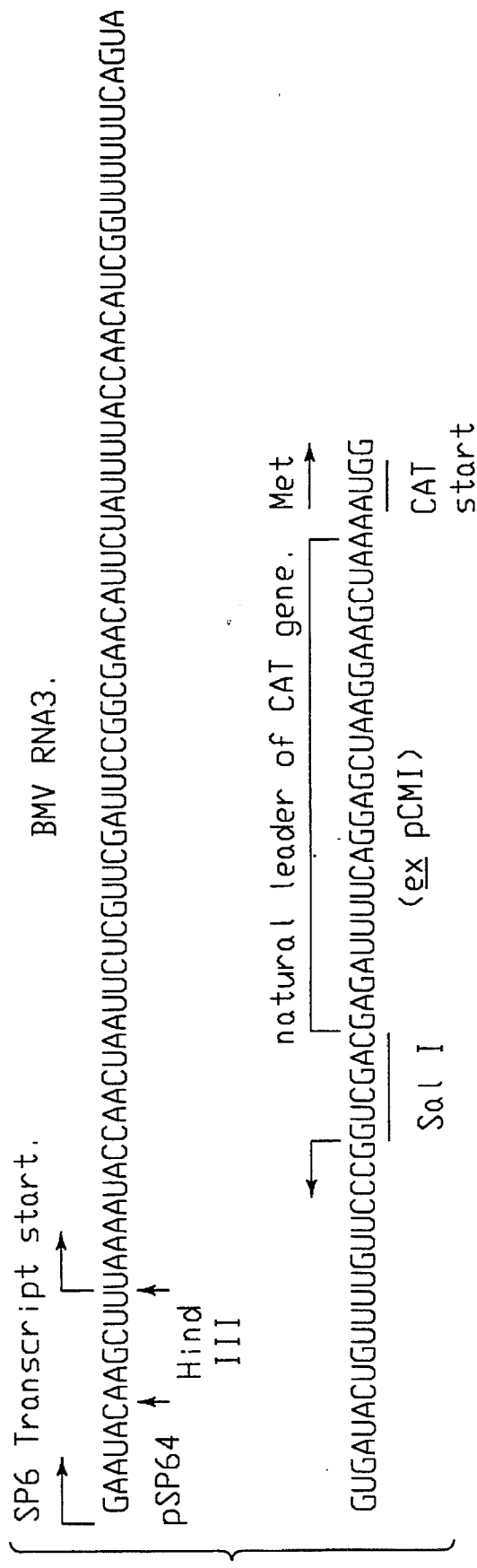
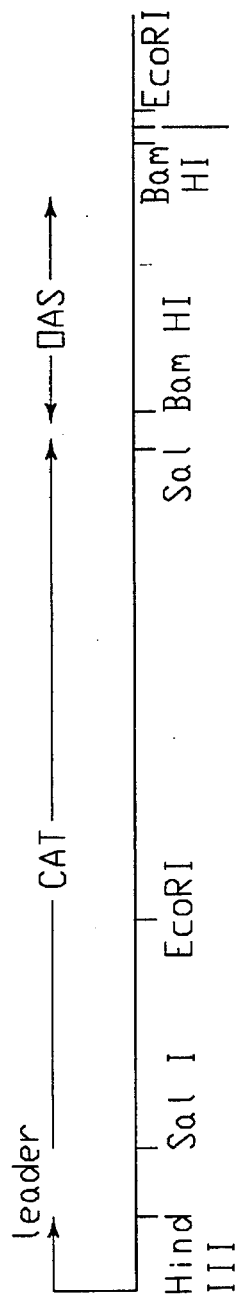
FIG. 7A
FIG. 7B

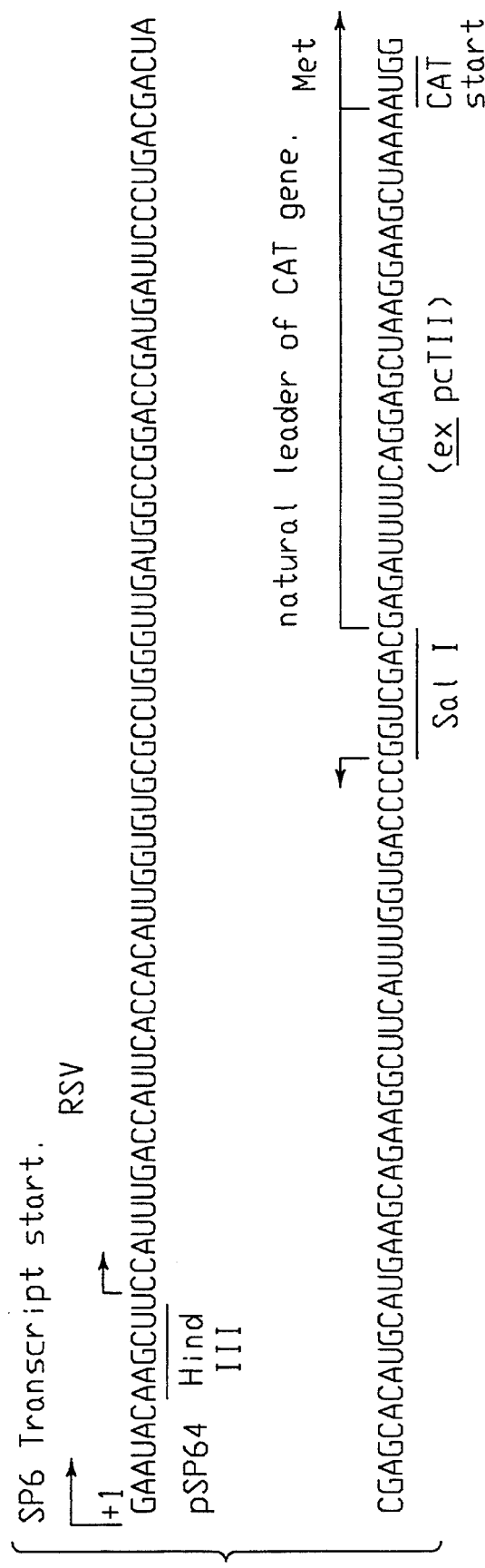
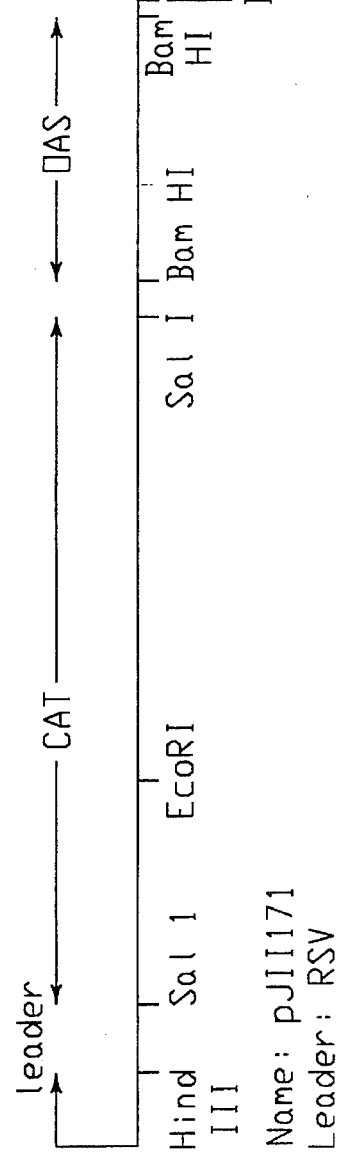
FIG. 8A
FIG. 8B

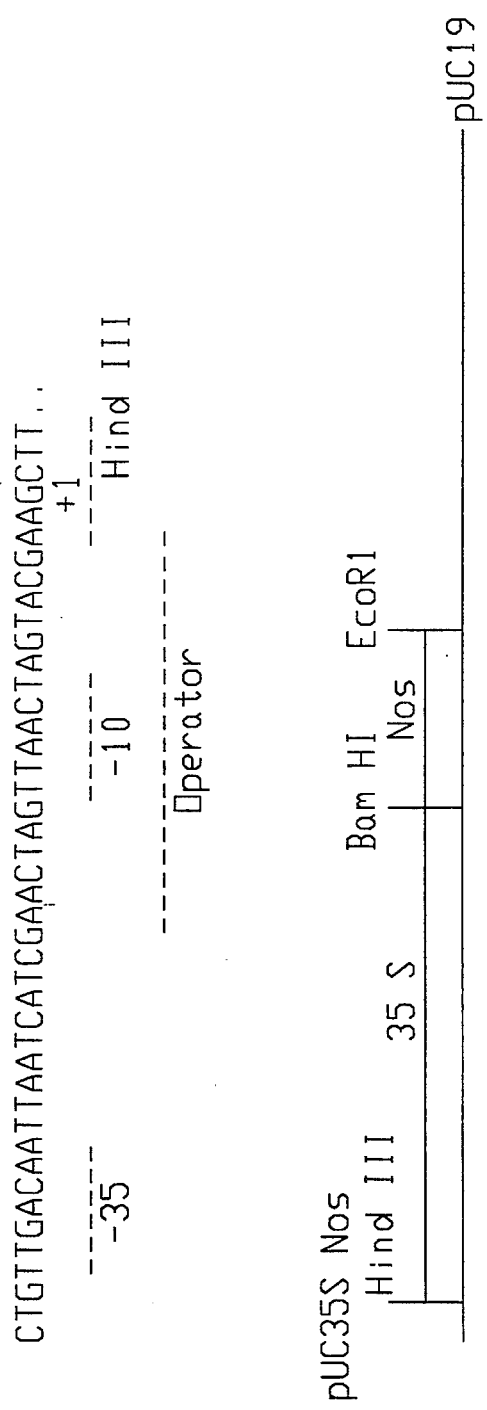
FIG. 18  Trp promoter and transcriptional start site.
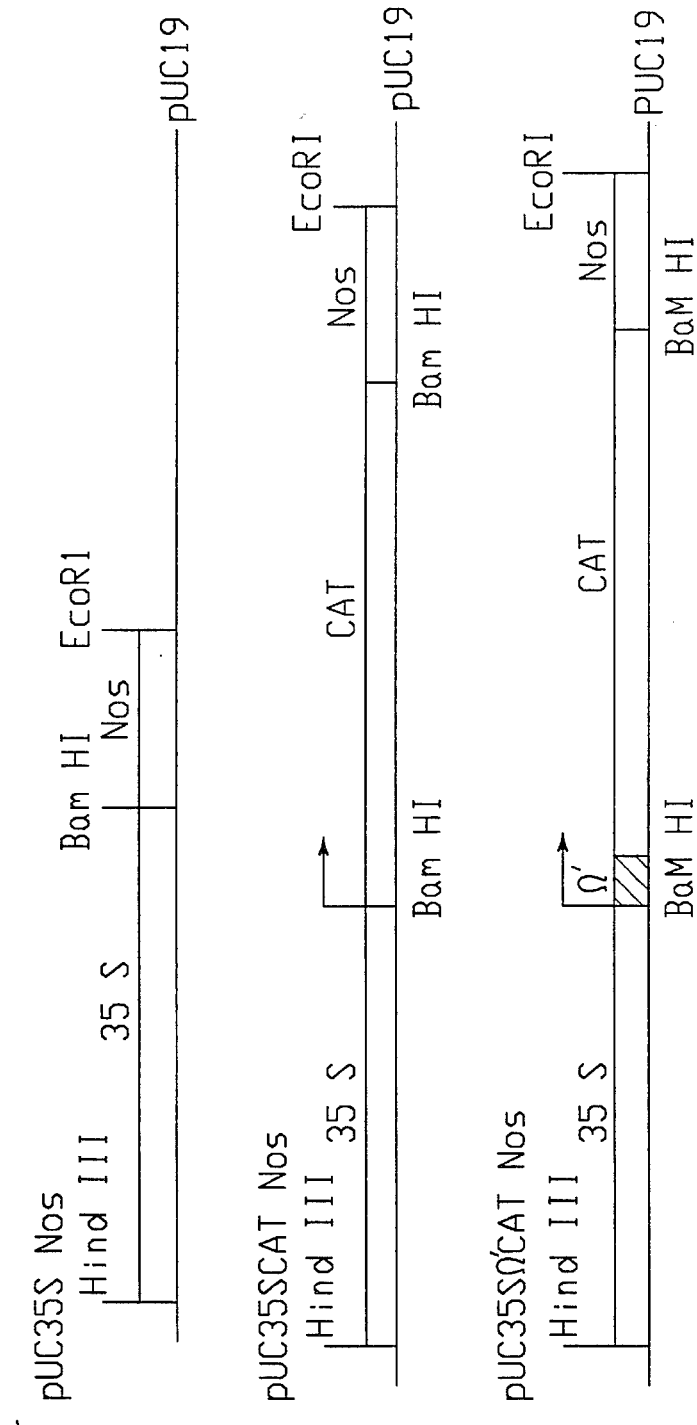
FIG. 19

5,489,527

TRANSLATION OF M-RNA

This application is a continuation of application Ser. No. 07/148,650, filed Feb. 4, 1988, abandoned, which was filed as International Application No. PCT/GB87/00390 on June 1987.

BACKGROUND OF THE INVENTION

This invention relates to enhancers of the translation of mRNA.

FIELD OF THE INVENTION

The mechanisms by which eukaryotes and prokaryotes initiate translation are known to have certain features in common and to differ in others. Eukaryotic messages are functionally monocistronic, translation initiates at the 5' end and is stimulated by the presence of a cap structure ($m^7G^5ppp^5G$...) at this end (Shatkin, Cell 9 645 (1976)). Prokaryotic messages can be polycistronic, can initiate at sites other than the 5' terminus, and the presence of a cap does not lead to translational stimulation. Both eukaryotes and prokaryotes begin translation at the codon AUG, although prokaryotes can also use GUG. Translation in both is stimulated by certain sequences near the start codon. For prokaryotes, it is the so-called Shine-Dalgarno sequence (a purine rich region 3–10 nucleotides upstream from the initiation codon). For eukaryotes, it is a purine at the −3 position and a G residue in the +4 position (where the A of the AUG start codon is designated +1), plus other sequence requirements involved in finer tuning. This is part of the "relaxed" version of the scanning model (Kozak, Nuc. Acids. Res. 12, 857 (1984)) whereby a 40S ribosomal sub-unit binds at the 5' end of the eukaryotic mRNA and proceeds to scan the sequence until the first AUG, which meets the requirements of the model, is encountered, at which point a 60S sub-unit joins the 40S sub-unit, eventually resulting in protein synthesis. Reference can be made in this connection to the following publications by Kozak: Cell 15, 1109 (1978), Nuc. Acid. Res. 9, 5233 (1981) and Cell 44, 283 (1986).

Beyond these sequence requirements in and about the initiation codon, there are no additional regions of mRNA which are known to enhance translation reproducibly.

During, eukaryotic transcription, sequences known as "enhancer" regions can provide transcriptional stimulation.

RNA viruses contain either positive or negative single-stranded RNA or double-stranded RNA. The class of RNA viruses include the majority of plant viruses (over 90%), some animal viruses and several bacteriophage.

One of the most widely studied of RNA viruses is tobacco mosaic virus (referred to hereinafter as TMV). The complete nucleotide sequence of TMV is known (Goelet et al., Proc. Natl. Acad. Sci. USA 79 5818 (1982)). The 5'-region of TMV RNA was first isolated in 1965 as an RNase $T_1$-resistant fragment 70 nucleotides long (Mundry, Z. Vererbungsl. 97, 281 (1965)) and free of internal G residues (Mandeles, J. Biol. Chem. 243, 3671). This region (later referred to as omega, Mandeles J. Mol. Biol. Chem. 243 3671) was sequenced (Richards et al. Euro. J. Biochem. 84 513 (1978)) and shown to form disome initiation complexes with wheat germ ribosomes. One ribosome occupies the AUG initiation site of the 126 KDa protein coding region and the second binds to the upstream leader sequence (Filipowicz and Haenni, Proc. Natl. Acad. Sci. USA 76, 3111 (1979); Konarska et al., Eur. J. Biochem. 114, 221 (1981)). Recent additional evidence to support the role of omega in ribosome association comes from the uncoating/gene expression data of Wilson and co-workers, (reviewed in J. Gen. Virol. 66, 1201 (1985) and UCLA Symp. 54 159 (1987)). It was observed in various in vitro translation systems that TMV particles are uncoated by the binding of ribosomes to the 5' end and their translational movement toward the 3' terminus.

SUMMARY OF THE INVENTION

It has now been found that the 5'-regions of RNA viruses act as enhancers of translation of mRNA.

According to a first aspect the present invention provides mRNA including the 5'-leader sequence of an RNA virus up to the first initiation codon of the viral RNA (or a derivative or portion thereof), the mRNA also including downstream sequence not derived from the virus providing the leader sequence.

According to a second aspect the invention provides a DNA sequence complementary to the 5'-leader sequence of an RNA virus, up to the first initiation codon of the viral RNA (or a derivative or portion thereof).

According to a third aspect the invention provides a DNA sequence comprising a promoter, a sequence complementary to the 5'-leader sequence of an RNA virus up to the first initiation codon of the viral RNA (or a derivative or portion thereof) and an open reading frame including an appropriate initiation codon. The invention also provides an expression vector including such a DNA sequence.

According to a fourth aspect the invention provides the use of the 5'-leader sequence of an RNA virus up to the first initiation codon of the viral RNA (or a derivative or portion thereof), either as RNA or as complementary DNA, as an enhancer of translation of mRNA when the 5'-leader RNA is contiguous with the mRNA.

BRIEF DESCRIPTION OF THE FIGURES

FIG. 5 Chimaeric RNA construct containing CAT mRNA with the 5' leader sequence from tomato TMV (SPS isolate);

FIG. 6 Chimaeric RNA construct containing CAT mRNA with the 5' leader sequence from TYMV;

FIG. 7 Chimaeric RNA construct containing CAT mRNA with the 5' leader sequence from BMV RNA 3;

FIG. 8 Chimaeric RNA construct containing CAT mRNA with the 5' leader sequence from RSV;

FIG. 18 Trp promoter modified to create a 3' Hind III site and a blunt 5' end;

FIG. 19 Constructs pUC35SCATNos and pUC35SVΩ'CATNos; and

DETAILED DESCRIPTION OF THE PREFERRED EMBODIMENTS

Figure 1A:
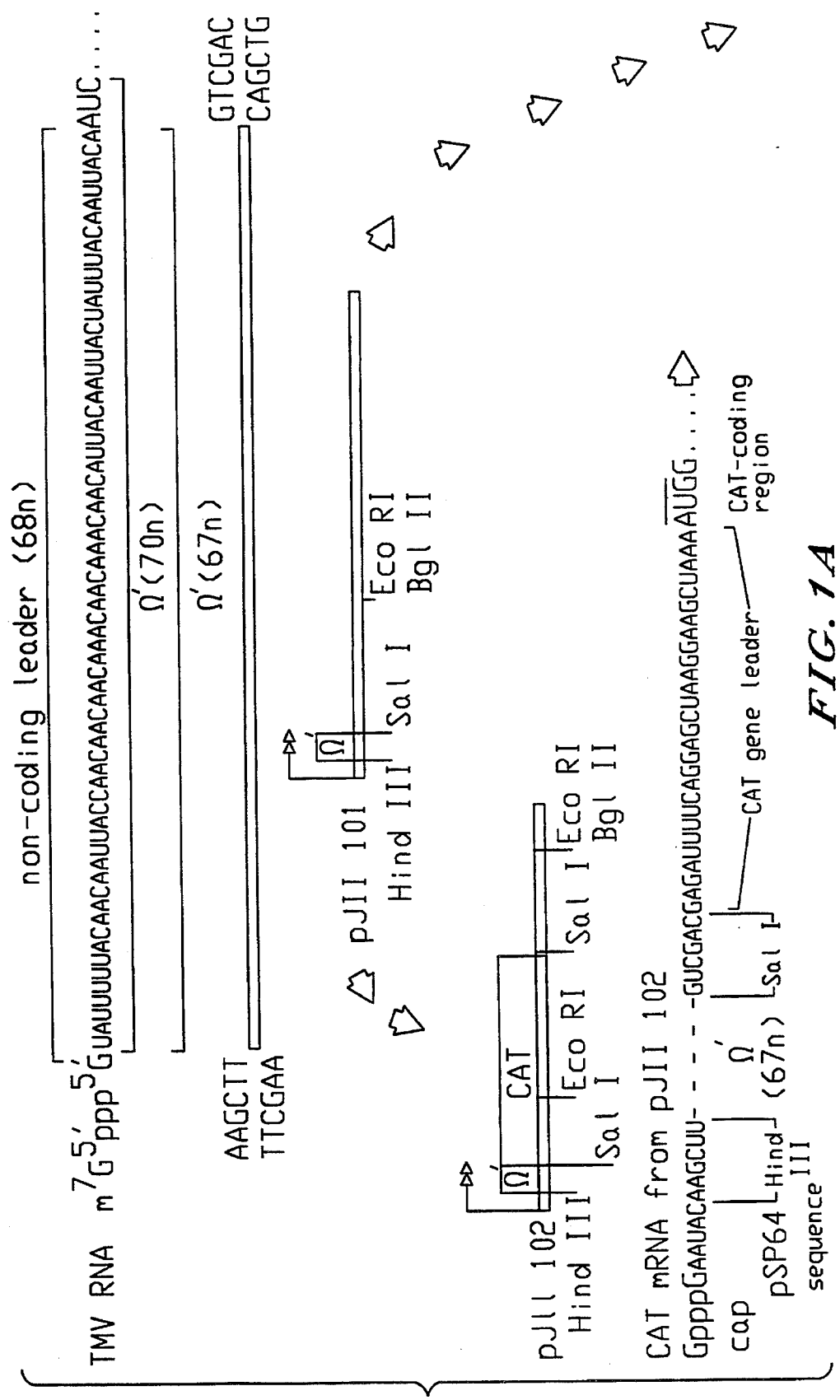
FIG. 1 Production of chimaeric mRNA containing Ω'.

Most RNA viruses which have been sequenced contain 5'-leader sequences, i.e. sequences at the 5'-end up to but not including the first initiation codon. Appropriate 5'-leader sequences from any RNA virus may be used as a translational enhancer according to the invention.

As noted above, the 5'-leader sequence of TMV plus the AUG initiation codon is known as omega and its nucleotide sequence is known (Richards et al. Eur. J. Biochem. 84, 513 (1978)) so that cDNA can be prepared synthetically. The omega prime (Ω', see FIG. 1) sequence of TMV represents the preferred translational enhancer according to the invention.

Information is also available about the translational enhancement by 5'-leader sequences of other RNA viruses including the following:

Turnip yellow mosaic virus genome RNA (Filipowicz and Haenni. Proc. Natl. Acad. Sci. USA 76 3111 (1979)), brome mosaic virus RNA 3, alfalfa mosaic virus RNA 4 (Goelet et al., Proc. Natl. Acad. Sci. USA 79 5818 (1982)); Rous Sarcoma virus (J. L. Darlix et al. Nuc. Acids Res. 10, 5183 (1982)).

In any particular case it will almost certainly be possible to vary the natural 5'-leader sequence in such a way that its function as a translational enhancer is modulated but not destroyed. Such variants are referred to herein as "derivatives" and derivatives of the natural sequence and their use as translational enhancers form part of the present invention. It may also be the case that parts only of the natural 5'-leader sequence (or a derivative sequence) are required to provide translational enhancement. Such parts of the sequence are referred to herein as "portions" and portions of the natural sequence or of derivatives thereof and their use as translational enhancers form part of the present invention.

In any particular case, determination of the nucleotide sequence of the 5'-leader of an RNA virus should be within the expertise of a man of ordinary skill in the art using known and readily available techniques. Similarly, identification of those parts of the natural 5'-leader sequence which are essential for translational enhancement and those which can be modified or omitted (i.e. the identification of derivatives and portions of the natural sequence) is a matter which can be determined by routine experimentation.

The 5'-leader sequences of RNA viruses (or derivatives or portions thereof) can be used as such as translational enhancers according to the invention by ligating them upstream of an appropriate mRNA using for example $T_4$ RNA ligase. The 5'-leader sequence may be immediately adjacent to the initiation codon of the downstream mRNA, or it may be spaced therefrom by an intervening sequence. However, it is preferred to use the 5'-leader sequence in the form of complementary DNA. The cDNA can be obtained in any manner which is desired. However in view of the relatively short length of the 5'-leader sequences in question it will usually be most convenient to synthesise the cDNA chemically. The cDNA will generally be incorporated into an expression vector. An expression vector is any vector capable of expressing those DNA sequences contained therein which are operably linked to other sequences capable of effecting their expression. An expression vector will usually contain a DNA sequence comprising a promoter, the sequence complementary to the 5'-leader sequence of an RNA virus up to but not including the first initiation codon of the viral RNA (or a derivative or portion thereof) and an open reading frame including an appropriate initiation codon. The open reading frame will generally code for one or more proteins of interest. The expression vector may be introduced directly into the host cell stably or transiently where the DNA sequence is expressed by transcription and translation. In the case of stable expression the vector must be replicable in the host either as an episome or as an integral part of the chromosomal DNA. Alternatively the expression vector can be transcribed in vitro and the RNA introduced directly into the cell for transient expression.

The translational enhancers according to the invention can be used in any situation where it is desired to enhance the translational efficiency of mRNA. However it should be noted that the effect of the enhancers is most marked in the case of an mRNA which is otherwise poorly translated. Thus the addition of either a cap or an enhancer according to the invention or both will stimulate translation. In the case of an mRNA already bearing a cap the effect of the enhancer according to the invention, is still present.

The translational enhancers according to the invention are effective in many different types of expression system, for example plant cells, bacteria and animal cells although a particular enhancer may be more suitable for one system rather than another. For example during testing in vitro the omega sequence of TMV appears to show a greater degree of enhancement in the wheat germ system and *E. coli* than in the rabbit *reticulocyte lysate* system although enhancement of translation is observed in all three system. The matching of particular enhancers to particular expression systems will generally be a matter well within the expertise of the man of ordinary skill.

In general the translational enhancers according to the invention can be used with advantage in any case where the value of an organism or cell line to commerce, including agriculture,is determined by the level of expression of one of its natural genes or of an artificially introduced gene.

(i) In the manufacture of commercially useful proteins in genetically engineered organisms or cell lines.

(ii) In fermentation where the rate of production of a product of intermediary metabolism catalysed by enzymes can be enhanced by increasing the rate of synthesis of a particular enzyme.

(iii) In viral cross-protection where the effects of a viral infection can be reduced by prior exposure to an attenuated form of the virus and it is advantageous to increase the level of protection by increasing the level of production of the component which provides the protection. For example plants can be protected against infection by TMV by exposing them to a genetically engineered strain of Agrobacterium which contains a cDNA copy of that portion of the TMV RNA which codes for the viral coat protein. Bacterial cDNA inserted in the plant genome continually expresses the coat protein which protects the plant against infection by the virus itself.

(iv) In the genetic engineering of plants where a property such as herbicide resistance is installed by artificial modification of the intermediary metabolism of the plant.

(v) In the expression of a partial clone of a gene, for example where it is desired to raise antibodies to the product of expression of the partial clone.

The invention is illustrated further by the following experimental work.

EXPERIMENTAL mRNA

Figure 1B:
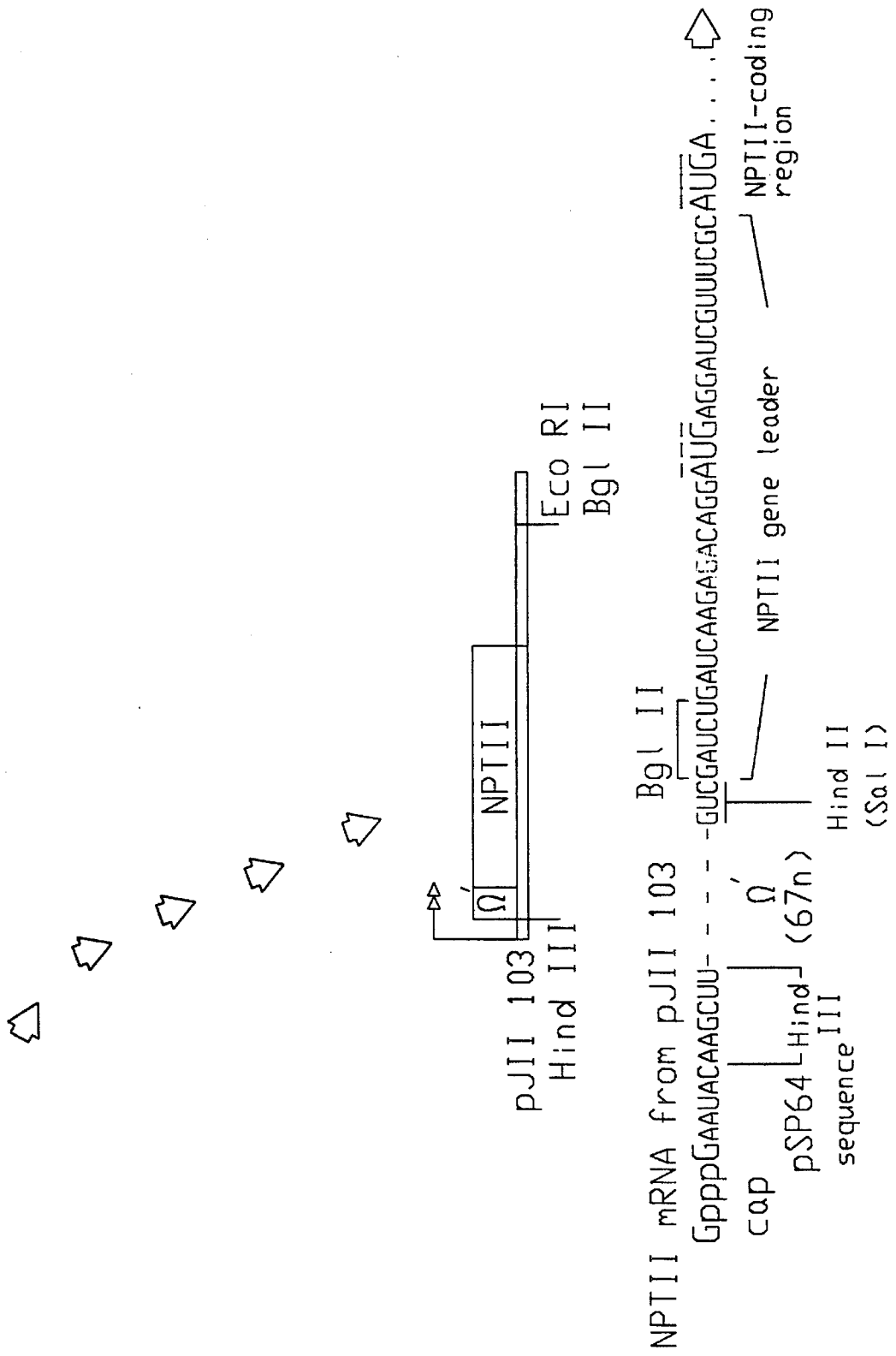

Chimaeric mRNA according to an embodiment of the invention was produced in the following manner, as illustrated in FIG. 1.

Using the sequence of TMV RNA vulgare strain (Goelet et al., Proc. Natl. Acad. Sci. USA 79 5818 (1982)), an 81 base oligonucleotide was synthesised containing the DNA sequence complementary to the 67 base sequence upstream of the AUG initiation codon of the 126 kDa open reading frame, but not including the 5' cap($m^7$Gppp and adjacent G residue). This sequence is called omega prime. A HindIII site was incorporated at the 5' end and a Sal I site at the 3' end of this oligonucleotide. A second oligonucleotide of 20 bases, including 13 bases at the 3' end of the omega prime sequence and a Sal I site, was synthesized as a primer for the synthesis of the second strand. After annealing, second strand synthesis was completed using the Klenow fragment of DNA polymerase I.

The resulting double-stranded 81 bp fragment was digested with HindIII/Sal I to create a 77 bp fragment with single-stranded cohesive ends and inserted into the corresponding sites of pUC19. The fact that the synthesis had resulted in the correct orientation of the omega prime sequence of TMV was verified by sequence analysis using the dideoxy chain termination method (Sanger et al., Proc. Natl. Acad. Sci. USA 74, 5463 (1977)). The fragment containing omega prime of TMV was then introduced into the HindIII/Sal I sites of plasmid pJII1 to result in pJII101. pJII1 is derived by inserting the TMV origin of assembly sequence as a BamHI fragment into the corresponding site of pSP64 (Melton, Nuc. Acids Res. 12 7035 (1984)) and modifying the SmaI site to a Bgl II site (Sleat et al., Virology 155, 299 (1986)).

A 779 bp Sal I ended fragment from pCM1 (Close and Rodriguez, Gene 20, 305 (1982)) containing the chloramphenicol acetyltransferase gene (CAT) of Tn9 was introduced into the Sal I site of pJII1 and pJII101, resulting in pJII2 and pJII102, respectively. A 1.2 kb Bgl II/Sal I fragment from pKNR-H (Gallie et al., J. Bacteriol. 161, 1034 (1985)) containing the neomycin phosphotransferase II gene (NPTII) of Tn5 was made blunt ended with Klenow fragment and introduced into the Acc I site of pJII1 and pJII101 to result in pJII3 and pJII103, respectively. Correct orientation of both the CAT and NPTII genes was verified by restriction fragment analysis.

After linearisation of pJII2 and pJII102 with Bgl II and pJII3 and pJII103 with EcoRI, RNA transcripts of each were made using SP6 RNA polymerase. Capped versions of each were also made using GpppG and SP6 polymerase reaction conditions which ensure comparable yields of capped transcripts. Equivalent yields of RNA from the capped and uncapped reaction and for the constructs with or without the omega sequence were verified by denaturing formaldehyde-agarose gels.

Equivalent amounts of the various CAT containing transcripts and the NPTII containing transcripts were added to the rabbit *reticulocyte lysate* (MDL), wheat germ S-30 (WG) and *E. coli* S-30 in vitro translation systems under standard reaction conditions. The resulting polypeptide products were labelled with $^{35}$S-methionine.

Figure 2:
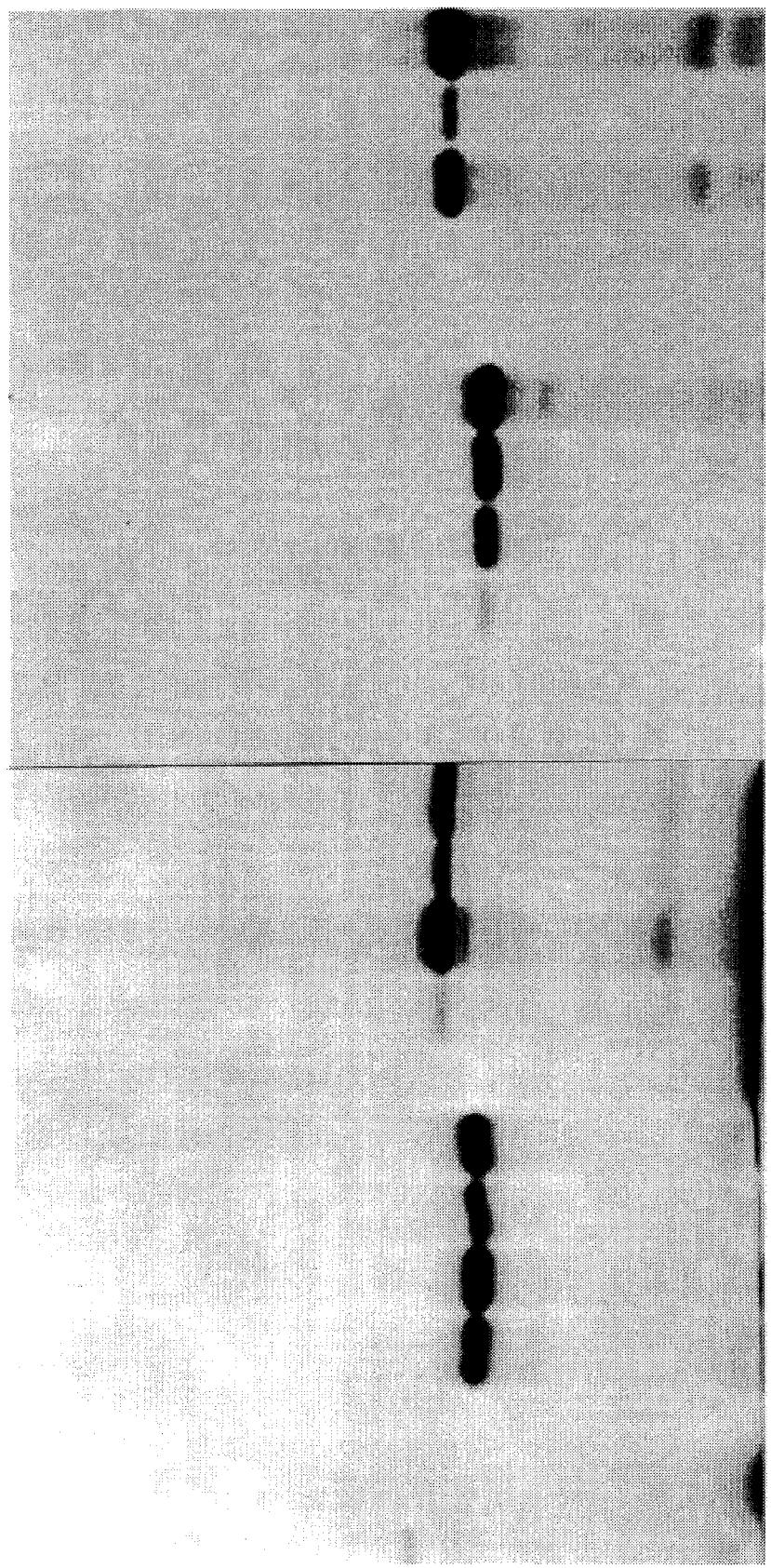
FIG. 2 SDS-PAGE analysis of translation products from MDL and WG.
Figure 3:
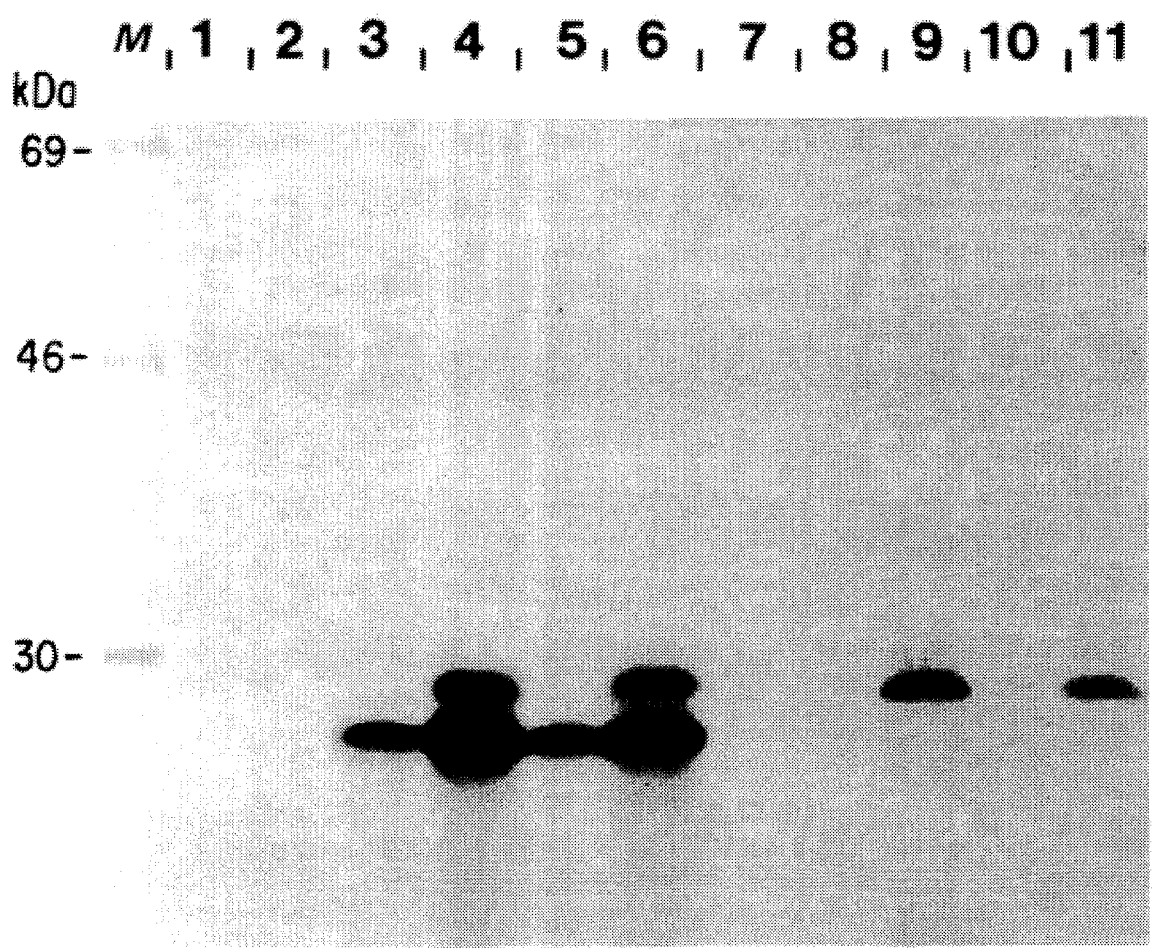
FIG. 3 SDS-PAGE analysis of translation products from *E. coli*.

FIGS. 2 and 3 show the SDS-PAGE analysis of the translation products from MDL (FIG. 2, tracks 1 to 11), WG (FIG. 2, tracks 12 to 22) and *E. coli* (FIG. 3). In FIG. 2 template additions were: tracks 1 to 12, $H_2O$ (endogenous translation); tracks 2 and 13, BglII-linearized pJII102 DNA; tracks 3 and 14, CAT RNA; tracks 4 and 15, omega prime-CAT RNA; tracks 5 and 16, 5'-capped CAT RNA; tracks 6 and 17, 5'-capped-omega prime-CAT RNA; tracks 7 and 18, EcoRI-linearized pJII103 DNA; tracks 8 and 19, NPTII RNA; tracks 9 and 20, omega prime-NPTII RNA; tracks 10 and 21, 5'-capped NPTII RNA; tracks 11 and 22, 5'-capped-omega prime-NPTII RNA. $^{14}$C-labelled marker proteins (Amersham International, plc) were loaded on track M. Their respective sizes in kilodaltons (kDa) are shown on the left. The dried gel was autoradiographed for 3 days at room temperature. In FIG. 3 template additions were: track 1, $H_2O$ (endogenous translation); track 2, BglII-linearized pJII102 DNA; track 3, CAT RNA; track 4, omega prime-CAT RNA; track 5, 5'-capped CAT RNA; track 6, 5'-capped-omega prime-CAT RNA; track 7, EcoRI-linearized pJII103 DNA; track 8, NPTII RNA; track 11, 5'-capped-omega prime-NPTII RNA. $^{14}$C-labelled marker proteins were loaded on track M and their sizes (in kDa) are shown on the left. The dried gel was autoradiographed for 3 days at room temperature. It should be noted that although the *E. coli* S-30 system is a transcriptionally active system, the native *E. coli* RNA polymerase does not recognise the SP6 promoter.

The following Table 1 shows the stimulating effect of the omega prime sequence. Zones from gels shown in FIGS. 2 and 3 were excised and the radioactivity in each band of product of translation was measured and the data normalised in each case to that from RNA not containing the omega prime sequence. Expressing the data in this way eliminates any stimulating effect of the cap alone and shows only the stimulating effect of the omega prime sequence.

TABLE 1

| mRNA | WG | MDL | E. coli |
| --- | --- | --- | --- |
| CAT | 1 | 1 | 1 |
| omega prime - CAT | 10 | 1.2 | 11 |
| GpppG - CAT | 1 | 1 | 1 |
| GpppG - omega prime - CAT | 3.8 | 2.2 | 2.7 |
| NPTII | 1 | 1 | 1 |
| omega prime - NPTII | 71 | 17.8 | 74 |
| GpppG - NPTII | 1 | 1 | 1 |
| GpppG - omega prime - NPTII | 9.5 | 1.9 | 9.6 |

DISCUSSION

The presence of the omega prime region of TMV stimulates the expression of transcripts containing either the CAT or NPT II sequences in either the capped or uncapped state.

Stimulation was most marked with the translationally inefficient NPTII transcripts. Thus, the Tn5 fragment containing the NPTII gene contains an additional AUG immediately upstream from the AUG start codon of the NPTII gene. In addition, the "Kozak rules" (see the papers by Kozak referred to above) would suggest that the region about the NPTII start codon constitutes a poor signal for translational initiation. As seen in WG and MDL (FIG. 2, lanes 8 and 19), the NPTII transcript without either a cap or omega prime functions poorly. The addition of a cap or omega prime improves translation although the presence of omega prime has a greater stimulatory effect than the presence of a cap alone. E. coli translational machinery, although not cap-dependent, is greatly stimulated by the presence of the omega prime sequence (FIG. 3, lanes 4, 6, 9 and 11). In E. coli, addition of a cap to the omega prime sequence on CAT or NPTII mRNA did little to enhance its translation whereas addition of omega prime to capped CAT or NPTII mRNA resulted in greater enhancement. CAT gene mRNA, even without a cap or the omega prime sequence, functions more efficiently in the eukaryotic systems. The first AUG from the 5' terminus is the start codon for CAT and the sequence in and about the start codon conforms well to the "Kozak rules". This is most evident in the MDL system where a much lower mRNA concentration was required to prevent exhaustion of the available $^{35}S$ methionine pool. Not surprisingly then, the presence of the omega prime sequence in CAT mRNA was less stimulatory. MDL is though less cap-dependent than WG, however the presence of a cap on the NPTII transcript had a slight stimulatory effect (FIG. 2, lanes 8 and 10), whereas its presence on the CAT transcript had little effect (FIG. 2, lanes 3 and 5). CAT mRNA alone was much less active in the WG system. As a result, the presence of either a cap or the omega prime sequence or both was highly stimulatory (FIG. 2, lanes 14 to 17). In WG, addition of a cap to the omega prime sequence on NPTII mRNA (FIG. 2, lanes 20 and 22) did little to enhance its translation whereas addition of omega prime to capped or uncapped NPTII mRNA (FIG 2, lanes 19 and 21) resulted in a greater enhancement.

Therefore the presence of the omega prime sequence enhances translation in both eukaryotic (MDL and WG) and prokaryotic system. This is consistent with the ability of TMV particles to be uncoated and the RNA translated by eukaryotic or prokaryotic translational machinery. The omega prime sequence often has a greater stimulatory effect on the expression of transcripts than does the presence of a cap alone. In addition, the omega prime sequence enhances translation under conditions where capping does not, e.g. in the prokaryotic and, to some extent, the MDL systems.

FURTHER EXPERIMENTAL WORK

Figure 4:
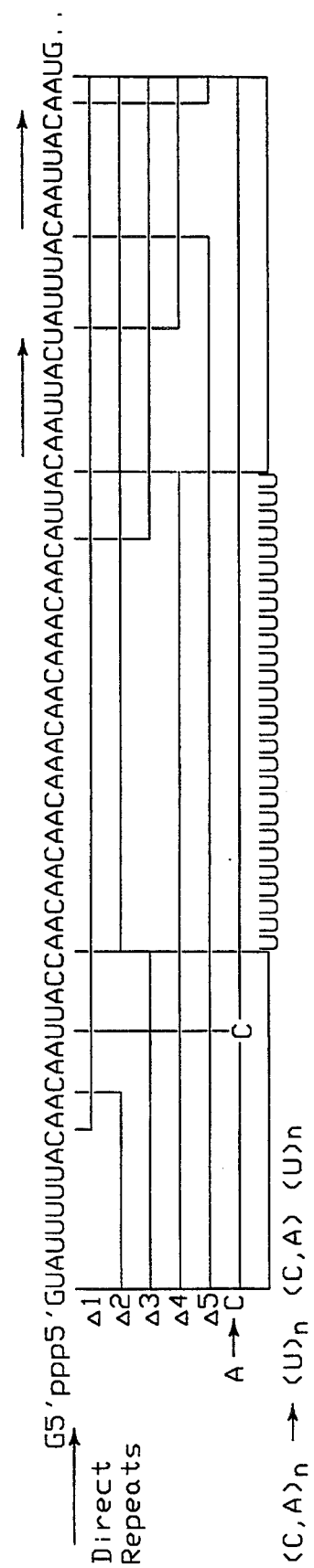
FIG. 4 Chimaeric RNA constructs containing mRNA and derivatives and portions of the Ω' leader sequence.
Figure 9A:
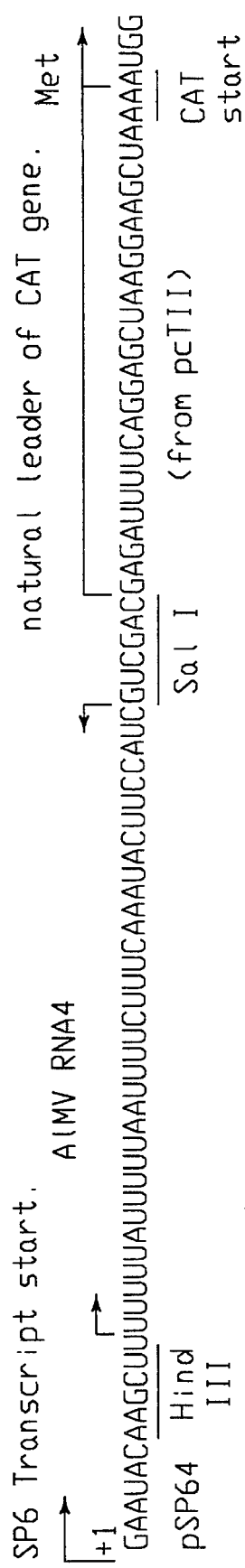
FIG. 9 Chimaeric RNA construct containing CAT mRNA with the 5' leader sequence from AlMV RNA 4.
Figure 9B:
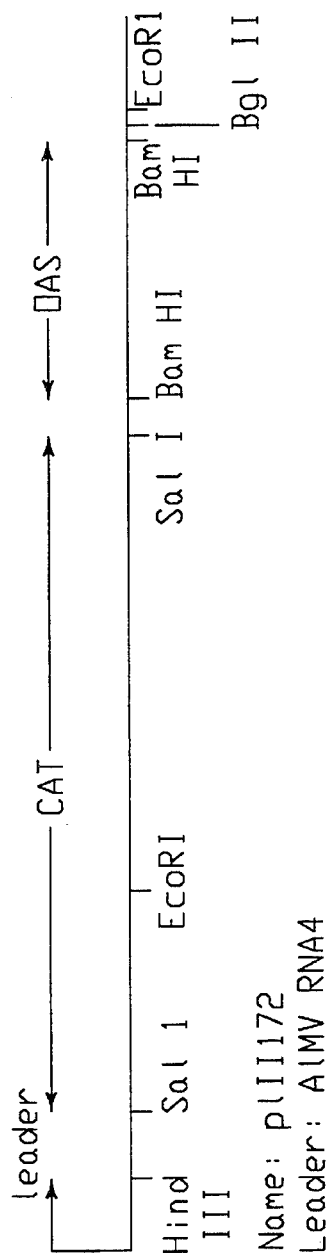
Figure 10A:
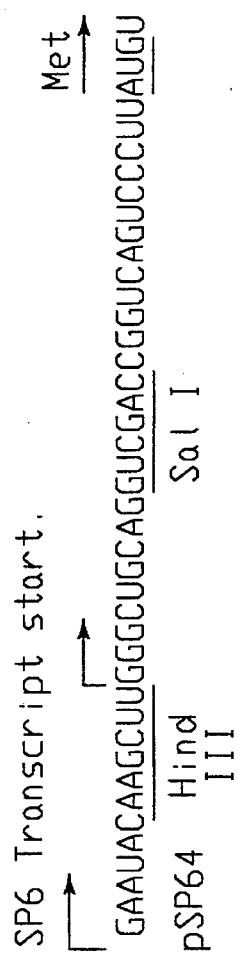
FIG. 10 Chimaeric RNA construct containing GUS mRNA (bad context) with the 5' leader sequence from pSP64 polylinker.
Figure 10B:
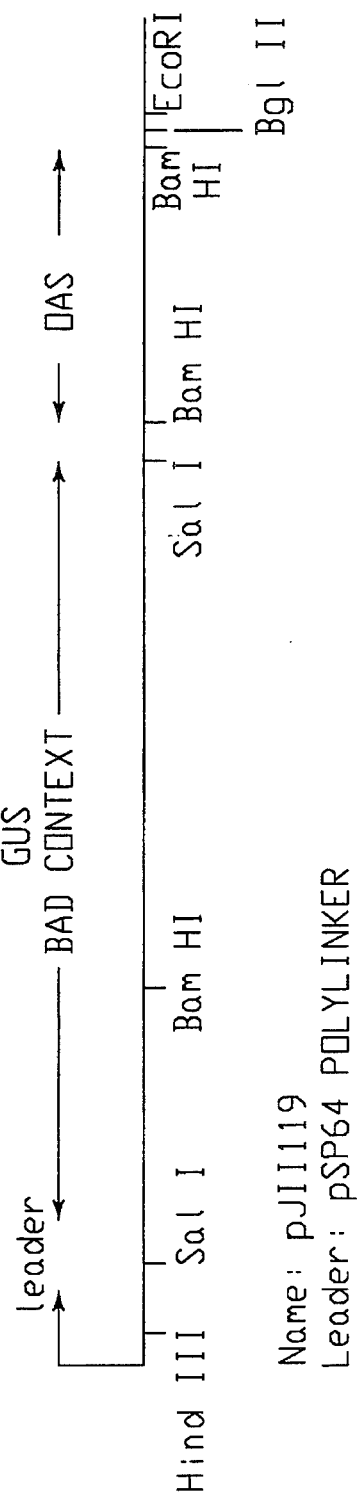
Figure 11A:
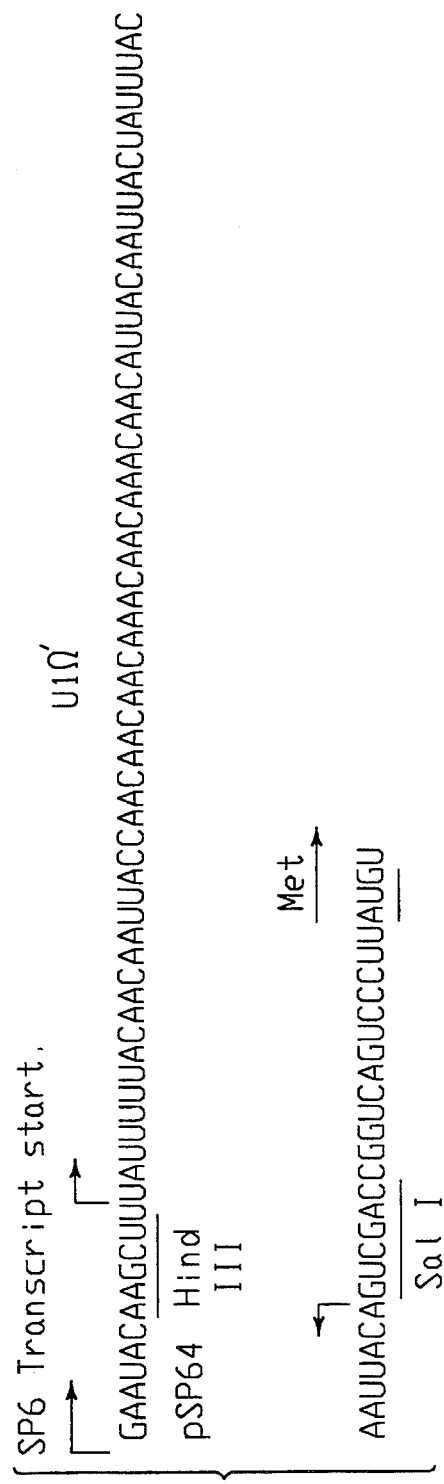
FIG. 11 Chimaeric RNA construct containing GUS mRNA (bad context) with the 5' leader sequence from U1-Ω.
Figure 11B:
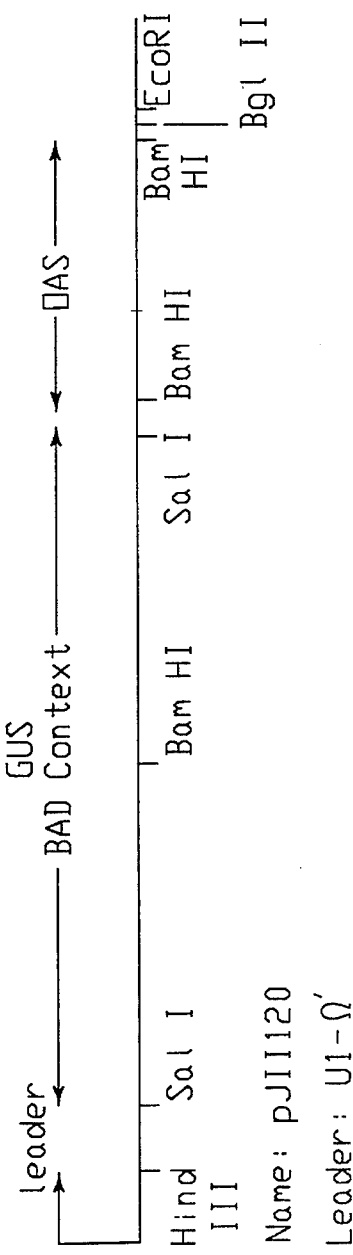
Figure 12A:
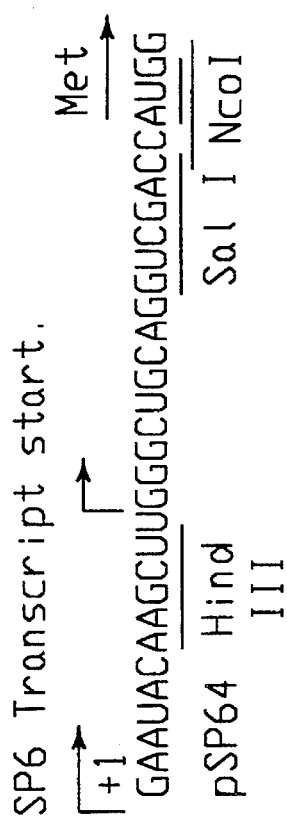
FIG. 12 Chimaeric RNA construct containing GUS mRNA (good context) with the 5' leader sequence from polylinker.
Figure 12B:
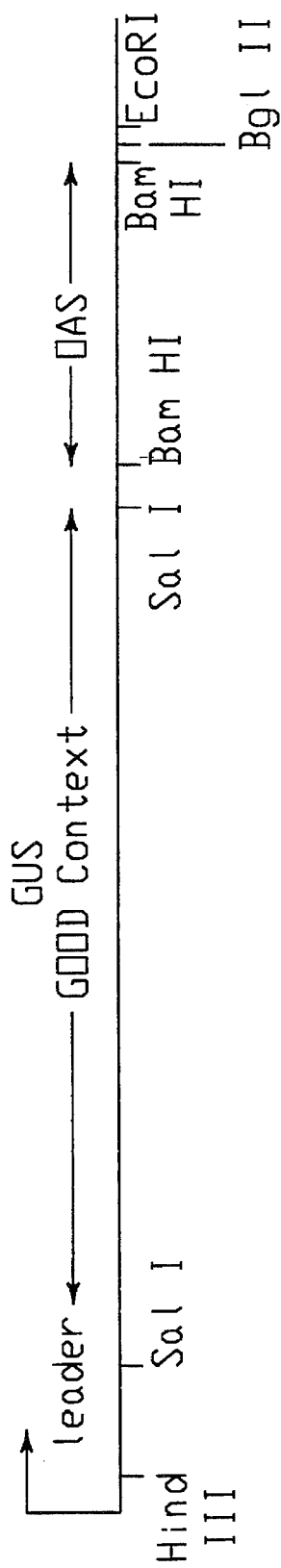
Figure 13A:
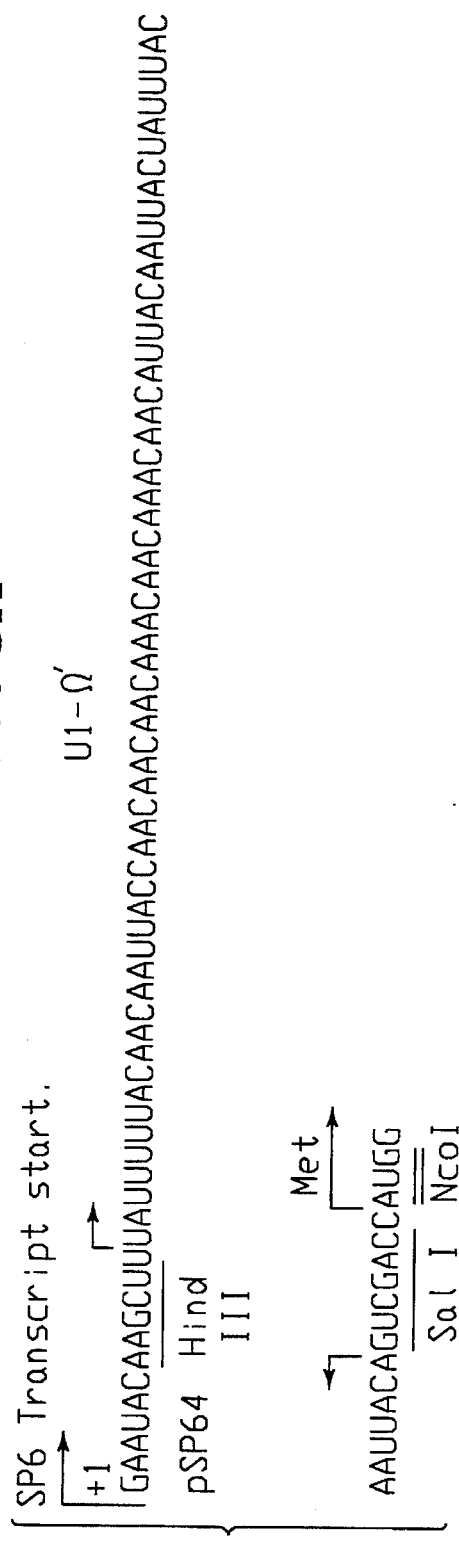
FIG. 13 Chimaeric RNA construct containing GUS mRNA (good context) with the 5' leader sequence from U1-Ω.
Figure 13B:
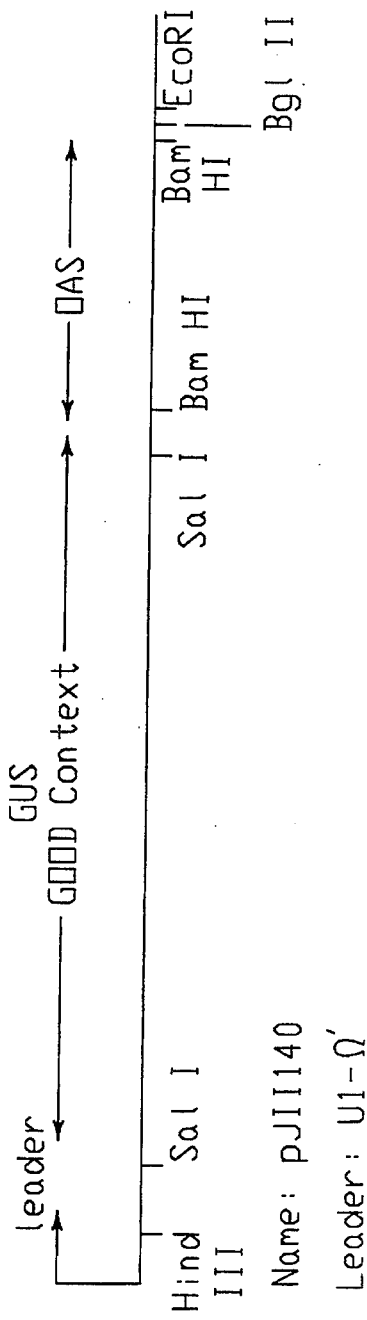

Chimaeric RNA constructs including CAT mRNA and derivatives or portions of the omega prime leader sequence were made in an analogous manner to that described above, the initial synthetic DNA sequence being chosen to produce the required RNA. As shown in FIG. 4, there were five deletions (referred to as Δ1 to Δ5), one A ->C transversion and one $[C,A]_n ->[U]_n$ substitution.

Further chimaeric RNA constructs containing CAT mRNA were made in an analogous manner with 5'-leader sequences of viruses other than TMV (U1, vulgare,or common strain), namely the tomato strain of TMV (SPS isolate), Turnip Yellow Mosaic Virus (TYMV), Brome Mosaic Virus RNA 3(BMV 3), Rous Sarcoma Virus partial leader (RSV) and Alfalfa Mosaic Virus RNA 4 (AlMV4). The initial DNA sequences synthesised and restriction site diagrams are shown respectively in FIGS. 5 to 9.

A further set of RNA constructs was prepared in an analogous manner, but the E. coli reporter gene β-glucuronidase (GUS) in place of CAT. The leader sequences used were either polylinker (for comparison purposes) or U2 omega (i.e. omega prime from TMV) or the derivatives and portions of omega prime and other viral leaders as described above. The GUS gene was used either in an artificial "good" Kozak context (see p. 33. re. Table 9) or in the native "bad" Kozak context as a SalI fragment from $_pRAJ235/240$ (Jefferson et al. Proc. Natl. Acad. Sci. 83, 8447 (1986)). The leader sequences and restriction site diagrams are shown in FIGS. 10 to 13. The expression of the reporter gene was determined fluorimetrically as described by Jefferson et al. Proc. Natl. Acad. Sci. 83 8447 (1986).

In addition to the three in vitro translation systems described above, two in vivo systems were used: microinjection of Xenopus laevis oocytes and electroporation of tobacco (Nicotiana tabacum cv Xanthi) mesophyll protoplasts. The respective techniques were as follows:

Two ng of each synthetic SP6 mRNA (or their corresponding DNA templates) were microinjected into the cytoplasm of stage 6 X. laevis oocytes in batches of 30 using standard procedures (Colman A. In Hames, B. D. and Higgins, S. J. (eds.), Transcription and Translation: A Practical Approach, IRL Press, Oxford, 271 (1984)). Oocytes were incubated for 18 hours in Modified Barths' Saline (MBS), then washed briefly in distilled water. Extracts from Xenopus oocytes were prepared by resuspending each sample in 0.25 M Tris-HCl, pH 7.4, containing 10 mM DTT (17 μl/oocyte), followed by sonication for 15 sec. Insoluble material was removed by microcentrifugation for 15 min. and fractions of the resultant extract representing equivalent numbers of ooctyes were assayed for CAT or GUS activity by published procedures (CAT Gallie et al. Nuc. Acids. Res. 15 3257 (1987); GIS: Jefferson et al. Proc. Natl. Acad. Sci. 83 8447 (1986)).

Mesophyll protoplasts were isolated from leaves of N. tabacum (cv. Xanthi) and stored in 0.7 M mannitol. The protoplats ($10^6$) were centrifuged at 60 xg for 3 min, resuspended in 1 ml ice-cold 0.7 M mannitol containing the RNA (8 μg), transferred to the electroporation cell and given a single voltage pulse (2.5kV/cm) by discharging a 50 nF capacitor through the cell. The pulse had a rapid rise-time (less than 1 μs) and an exponential decay with a half-life of about 5 μs. Electroporated protoplasts were stored at 0°–4° C. for 10 min. Ten mls of 0.7 M mannitol were added and the protoplasts recovered by centrifugation at 60 xg for 3 min. The protoplasts were then resuspended in culture medium and incubated at 25° C. for 21 hours in 9 cm-diameter Petri dishes.

Each sample of electroporated protoplasts was sedimented, resuspended and sonicated in 150 μl of 0.25 M Tris-HCl, pH 7.4 containing 2 mM leupeptin and 10 mM dithiothreitol (DTT) for CAT assays or 50 mM sodium phosphate pH 7.0, 10 mM 2-mercapto ethanol for GUS assays. Extracts were microcentrifuged at 10,000 xg for 10 min at room temperature of 4° C.

Figure 14:
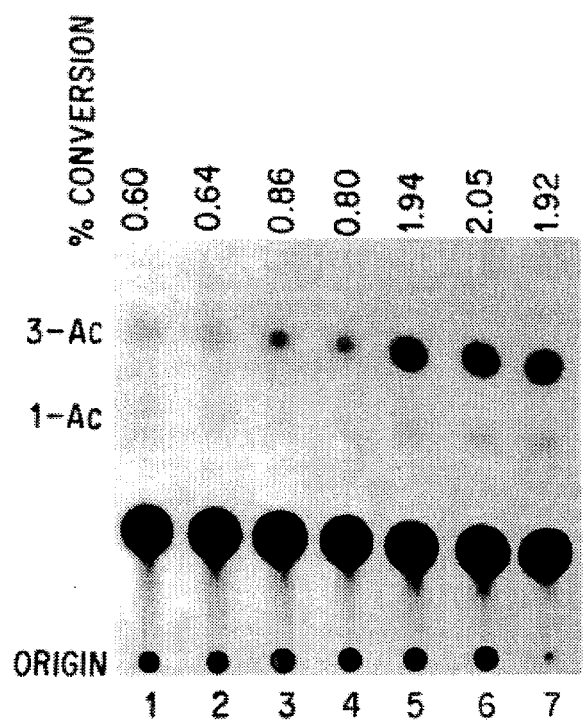
FIG. 14 Effect of Ω' on the expression of capped or uncapped CAT RNAs in electroporated tobacco protoplasts.

FIG. 14 shows the effect of omega prime on the expression of capped or uncapped CAT RNAs in electroporated tobacco protoplasts. Each origin spot received extract equivalent to $5 \times 10^4$ viable protoplasts. For each sample, the conversion (%) of substrate ($^{14}$C-chloramphenicol) into its mono-acetylated forms (indicated on the let) is shown at the top of the track. Electroporated RNAsor standards were:

track 1, no RNA (mock); track 2, CAT RNA; track 3, omega prime-CAT RNA; track 4, 5'-capped CAT RNA; track 5, 5'-capped-omega prime-CAT RNA; track 6, 0.1 unit purified CAT enzyme added to an equivalent volume of extract as for track 1;track 7, 0.1 unit purified CAT enzyme alone. The dried tlc plate was autoradiographed for 2 days before removing and determining the radioactivity in the releant $^{14}$C-labelled spots of mono-acetylated products (3-Ac/1-Ac), % conversion data reflects the relevant CAT activity in the extract. Omega prime (+/– a 5'-cap) was the most stimulatory of CAT RNA expression.

Figure 15:
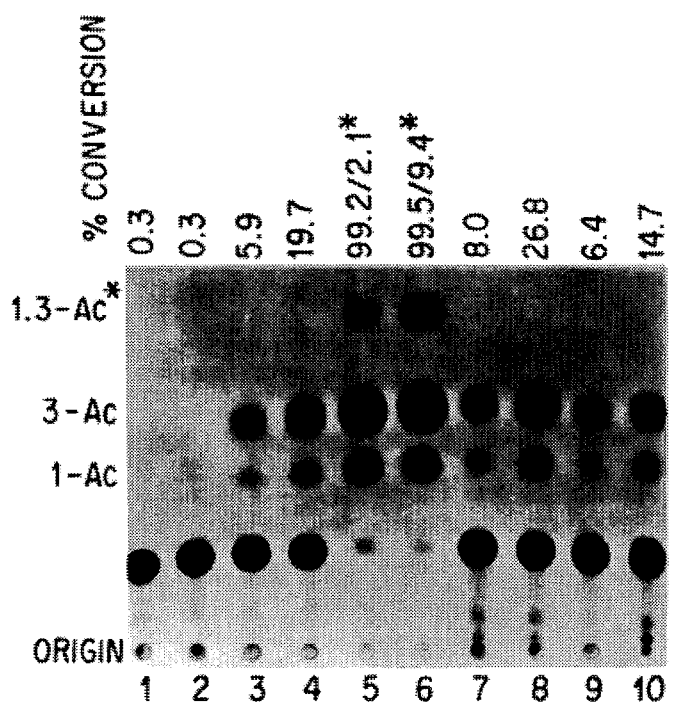
FIG. 15 Effect of Ω' on the expression of capped or uncapped CAT RNAs microinjected into *X. laevis* oocytes.
Figure 16A:
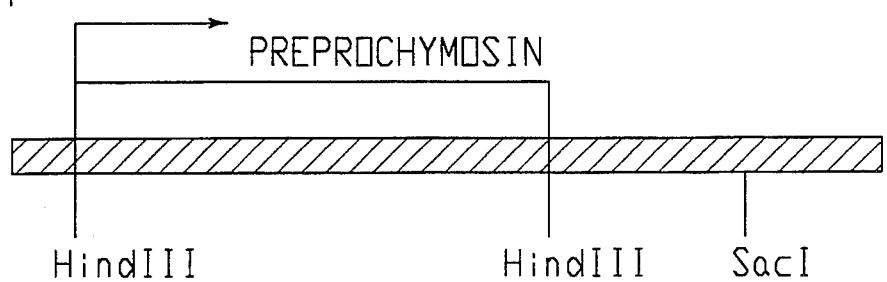
FIG. 16 Plasmids pJII6, pJII7.
Figure 16B:
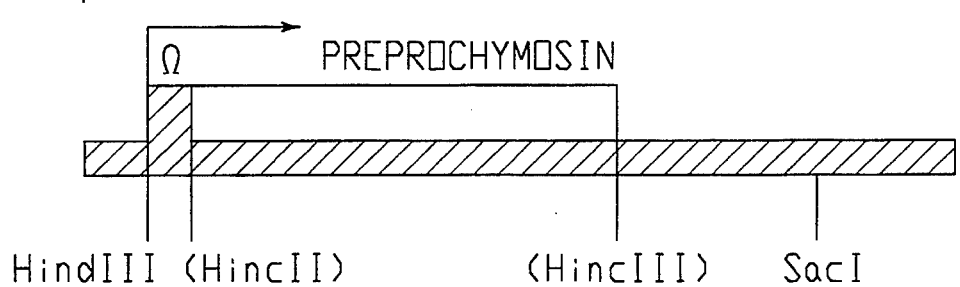
Figure 16C:
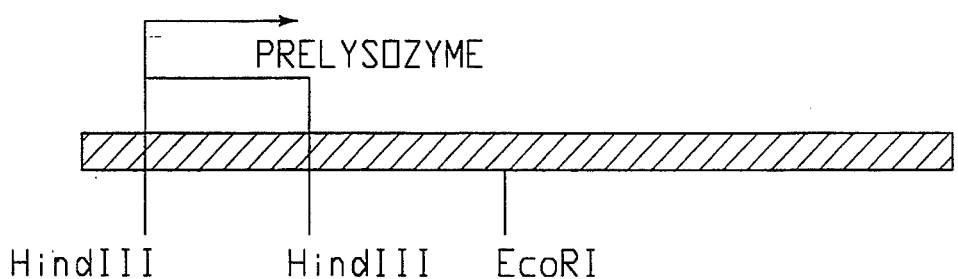
Figure 16D:
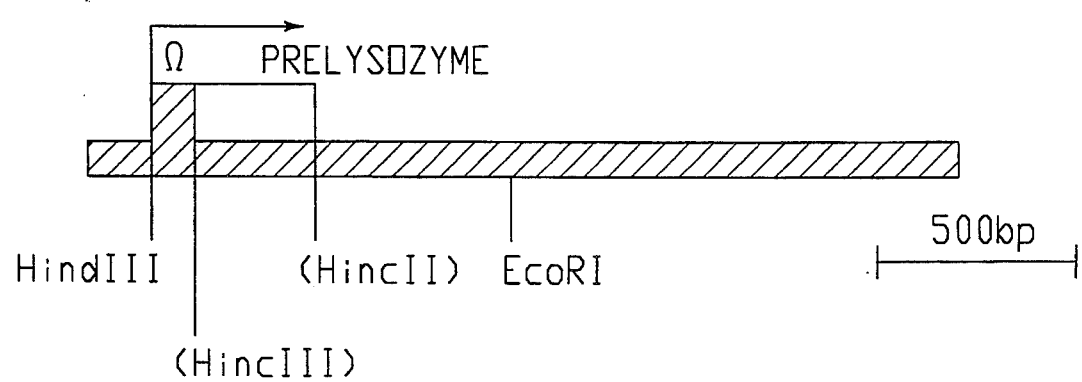
Figure 17A:
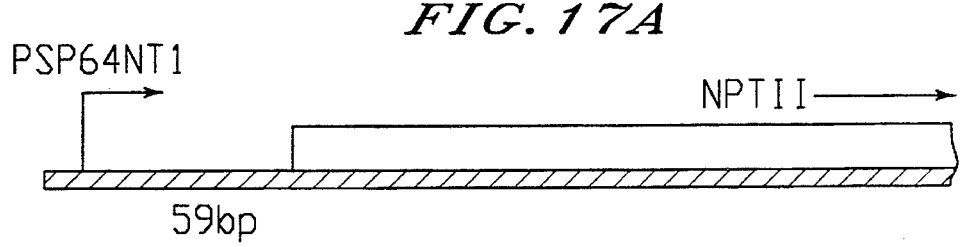
FIG. 17 Chimaeric RNA constructs with the NPT II coding region and either Ω', two tandem Ω' regions, a long (77 base) "junk" leader (polylinker) sequence or "junk" together with a central Ω'.
Figure 17B:
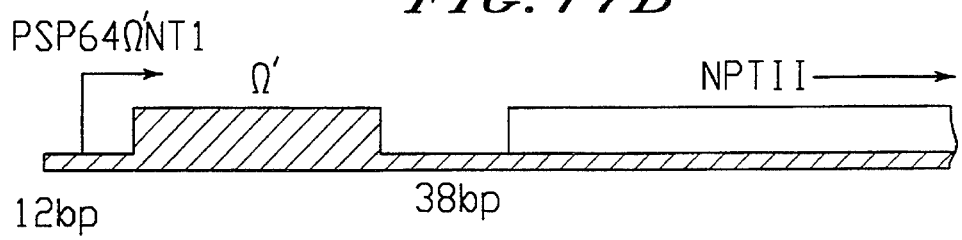
Figure 17C:
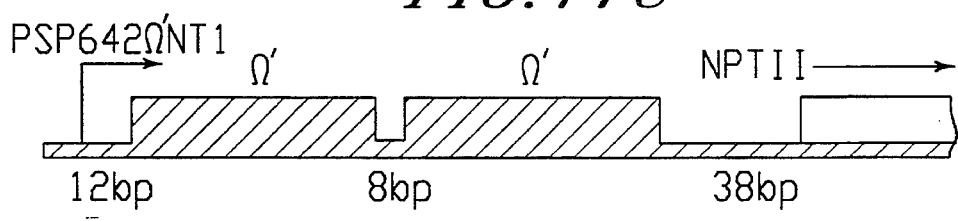
Figure 17D:
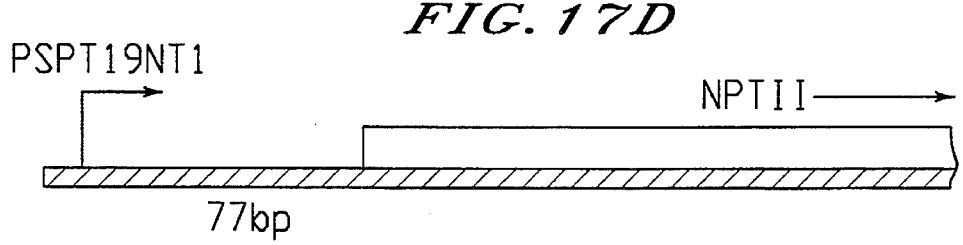
Figure 17E:
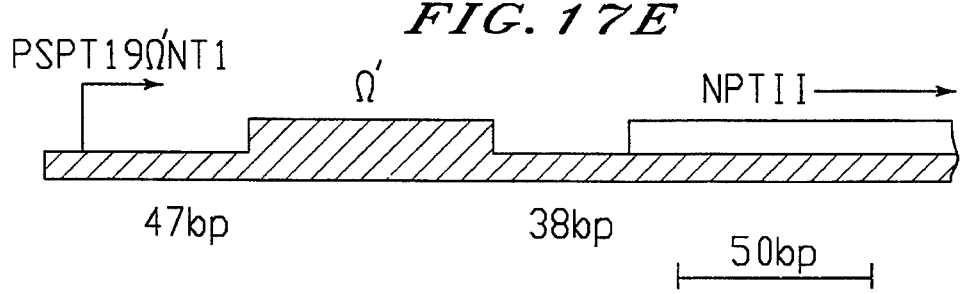

FIG. 15 shows the effect of omega prime on the expression of capped or uncapped CAT RNAs microinjected into X laevis oocytes. An equal amount of each CAT RNA-construct or linearized DNA template (2 ng) was injected per oocyte, throughout. Equal oocyte extract volume (equivalent to 0.3×cell) were assayed in each case, unless stated otherwise. Conversion (%) of $^{14}$C-chloramphenical into its mono-acetylated forms, is shown at the top of each track. In tracks 5 and 6, conversion (%) into the di-acetylated form is indicated by *. Microinjected RNAs or standards were: track 1, no RNA (mock); track 2, BglII-linearized pJII102; track 3, CAT RNA; track 4, omega prime-CAT RNA;track 5, 5'-capped CAT RNA; track 6, 5'-capped-omega prime-CAT RNA; track 7, as for track 5 but 20-fold diluted extract; track 8, as for track 6 but 20-fold diluted; track 9, 0.1 unit purified CAT enzyme added to an equivalent volume of extract as in track 1; track 10, 0.1 unit purified CAT enzyme alone. The dried tlc plate was autoradiographed at room temperature for 18 hours, before excising and counting the relevant $^{14}$C-labelled spots.

The following Tables show the further results obtained.

TABLE 2

Effect of deletions and other sequence alterations on translational enhancement by omega prime. Chloramphenicol acetyltransferase expression in RNA-microinjected Xenopus oocytes.

| RNA injected | % conversion of $^{14}$C-chloroamphenicol to the 1- and 3-monoacetylated forms |
|---|---|
| Nil (mock) | 0.1 |
| CAT | 4.5 |
| Omega prime CAT | 34.2 |
| Δ1 - CAT | 17.2 |
| Δ2 - CAT | 9.7 |
| Δ3 - CAT | 17.6 |
| Δ4 - CAT | 14.6 |
| Δ5 - CAT | 17.9 |
| A → C transversion - CAT | 15.7 |
| [(C,A)$_n$ → [U]$_n$ substitution - CAT | 34.3 |
| 0.1 units CAT (pure enzyme) | 1.2 |
| All RNA's were uncapped | |

The above results show that omega prime enhances translation of CAT. Deletion 1 to 5 reduce this effect without destroying it entirely. The same is true of the A->C transversion. The [U]$_n$ substitution has little effect, if any.

TABLE 3

Effect of untranslated 5'-leader sequences from different viruses on the level of expression of chloramphenicol acetyltransferase after microinjection of mRNA into Xenopus oocytes.

| RNA injected | % conversion of $^{14}$C-chloroamphenicol to the 1- and 3-monoacetylated forms |
|---|---|
| Nil (mock) | 0.1 |
| CAT | 6.3 |
| Omega U1 CAT | 46.5 |
| Omega (SPS) CAT | 35.8 |
| TYMV CAT | 1.3 |
| BMV3 CAT | 5.0 |
| RSV CAT | 5.4 |
| A1MV4 | 6.7 |
| 0.1 Units CAT (pure enzyme) | 1.3 |
| All RNAs were uncapped | |

Omega U1 derives from the standard strain of TMV (Vulgare). Omega SPS is from the tomato strain of TMV.

TYMV: turnip yellow mosaic virus leader.

BMV3: brome mosaic virus RNA3.

RSV: a partial leader sequence from Rous Sarcoma virus.

AlMV4: alfalfa mosaic virus RMA4.

The above results show that omega prime from TMV U1 enhances translation of CAT RNA in this system. TMV tomato strain omega prime also does so, but a little less well. Other viral leaders have little or no effect, TYMV leader may be inhibitory.

TABLE 4

Effects of different 5'-non-translated leader sequences with or without a 5'-cap on in vitro translation of chloramphenicol acetyltransferase mRNA in a wheat germ cell-free system. (The results as shown below have been normalized to the unmodified CAT mRNA leader sequence which was taken as 1.0 to show fold-stimulation over CAT mRNA alone).

| RNA added | Uncapped | capped |
|---|---|---|
| CAT | 1.0 | 1.0 |
| Omega prime CAT | 2.8 | 3.7 |
| Δ1 - CAT | 1.2 | 0.6 |
| Δ2 - CAT | 2.0 | 1.8 |
| Δ3 - CAT | 1.5 | 1.3 |
| Δ4 - CAT | 3.0 | 1.5 |
| Δ5 - CAT | 1.5 | 0.7 |
| A → C transversion - CAT | 3.3 | 2.9 |
| [C,A]$_n$ → [U]$_n$ substitution - CAT | 2.1 | 3.4 |
| TMV Tomato strain Omega prime - CAT | 1.7 | 3.0 |
| TYMV - CAT | 0.3 | 3.0 |
| BMV3 - CAT | 1.4 | 2.8 |
| RSV - CAT | 0.6 | 2.5 |
| A1MV4 - CAT | 2.1 | 2.3 |

Note: these figures represent comparisons of proportional stimulations of translation produced by the inclusion of different sequences at the 5' end of the CAT message. Translations were done with capped or with uncapped messages. Each column represents the yield of radioactive CAT protein recovered by excision from an independent gel (as in FIGS. 2 and 3). The bands were cut out, counted, and have been normalised to a band for which the mRNA was unmodified CAT message.

The above results show that omega prime enhances in this system, with or without 5'-capping. The other viral leader sequences and derivatives or portions of omega prime enhance translation to varying extents, but rarely significantly more than omega prime itself.

TABLE 5

Effects of different non-translated leader sequences, all without a 5'-cap structure, on in vitro translation of chloramphenicol acetyltransferase mRNA in an *E. coli* cell-free system.

| RNA added | Uncapped |
|---|---|
| CAT | 1.0 |
| Omega prime CAT | 9.0 |
| Δ1 - CAT | 3.3 |
| Δ2 - CAT | 2.5 |
| Δ3 - CAT | 6.3 |
| Δ4 - CAT | 4.2 |
| Δ5 - CAT | 3.8 |
| A → C transversion CAT | 4.1 |
| $[C,A]_n \to [U]_n$ substitution CAT | 1.9 |
| TMV Tomato strain Omega CAT | 6.6 |
| TYMV CAT | 0.2 |
| BMV3 CAT | 3.7 |
| RSV CAT | 1.5 |
| A1MV4 CAT | 1.4 |

The above results show that omega prime, some of its derivatives, and tomato strain prime enhance translation to the greatest extent. Most of the other sequences also enhance, but to varying extents. *E. coli* does not require a 5' cap for translation.

TABLE 6

Effect of different leaders on the translation of β-glucuronidase mRNA from $_p$RAJ235/240) electroporated into tobacco protoplasts.

| GUS mRNA construct used* | nmoles 4-methyl umbelliferyl glucuronide cleaved min$^{-1}$/μg protein in protoplast extract | Fold Stimulation |
|---|---|---|
| [Blank] (no mRNA) | — | — |
| Uncapped Leader | | |
| 235 [SP6 transcript, polylinker leader.] | <0.01 | 1 |
| Omega prime (U1) - 235 | 0.25 | >25 |
| Omega prime (SPS) - 235 | 0.15 | >15 |

TABLE 6-continued

Effect of different leaders on the translation of β-glucuronidase mRNA from $_p$RAJ235/240) electroporated into tobacco protoplasts.

| GUS mRNA construct used* | nmoles 4-methyl umbelliferyl glucuronide cleaved min$^{-1}$/μg protein in protoplast extract | Fold Stimulation |
|---|---|---|
| 235 | | |
| TYMV - 235 | <0.01 | — |
| A1MV4 - 235 | <0.01 | — |
| BMV3 - 235 | <0.01 | — |
| RSV - 235 | <0.01 | — |
| Capped Leader | | |
| capped 235 [SP6 transcript polylinker leader] | 0.03 | 1 |
| capped Omega prime - 235 | 0.54 | 18 |
| capped Omega prime (SPS) - 235 | 0.43 | 14 |
| capped TYMV - 235 | <0.01 | — |
| capped A1MV4 - 235 | 0.23 | 8 |
| capped BMV3 - 235 | 0.23 | 8 |
| capped RSV - 235 | 0.21 | 7 |
| capped Δ1 - 235 | 0.55 | 18 |
| capped Δ2 - 235 | 0.50 | 17 |
| capped Δ3 - 235 | 0.32 | 11 |
| capped Δ4 - 235 | 0.54 | 18 |
| capped Δ5 - 235 | 0.54 | 18 |
| capped A → C transversion - 235 | 0.69 | 23 |
| capped $[C,A]_n \to [U]_n$ substitution - 235 | <0.01 | — |

(blank value subtracted from all others)

(*Constructs were "bad" GUS ex pRAJ 235/240, with or without a 5' cap)

All mRNA constructs were electroporated at 8 μg/ml and washed protoplasts incubated for 20 hours as described (Gallie et al Nuc. Acids. Res. 15, 3257 (1987)).

The sequence of the "Bad" Kozak construct (235) leader is as follows:

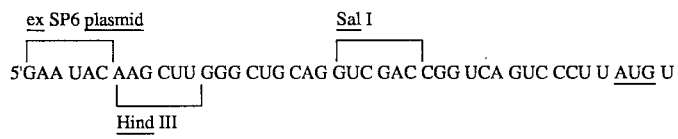

The insertion of Omega prime into the polylinker is as below:

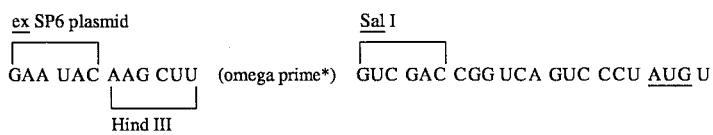

*wherein omega prime sequence is as below:-
UAU UUU UAC AAC AAU UAC CAA CAA CAA CAA ACA ACA AAC AAC AUU ACA AUU ACU AUU UAC AUU UAC A and the deleted omega prime derivatives, etc follow accordingly.

Messenger RNAs encoding calf preprochymosin or chicken prelysozyme were synthesized in vitro, with or without the TMV 5'-terminal sequence (omega prime). The mRNAs were translated in vitro in the systems derived from rabbit reticulocytes (MDL), wheat-germ (WG) or *E. coli* (EC).

The plasmids pJII6 and pJII7 (FIG. 16) were constructed using components of plasmids pSP64CT and pSP64LT (Sleat et al. Virology, 155 299 (1986)) and pJIII01. Both pJII6 and pJII7 are derivatives of the transcription plasmid pSP64 (Melton, 1984), which contains a promoter for the bacteriophage SP6 RNA polymerase adjacent to the polylinker sequence derived from M13 mp11. The preprochymosin and prelysozyme coding regions of pSP64CT and pSP64LT respectively were excised as HindIII fragments, blunt-ended with the Klenow fragment of DNA polymerase 1, and cloned into the HincII site of pJIII01 to generate pJII6 and pJII7 respectively (FIG. 16). These constructs were used to direct the synthesis of messenger-sense preprochymosin and prelysozyme transcripts bearing a 5'-terminal omega prime sequence. Parental plasmids pSP64CT and pSP64LT were templates for synthesis of mRNAs lacking omega prime.

The results are shown in Table 7 below.

TABLE 7

Effect of omega prime on expression of two eukaryotic mRNAs in 80S- and 70S-ribosome-based translation systems. Incorporation of L-[$^{35}$S]-methionine (cpm) into gel-purified polypeptides.

| | CPM (Rel. Stimulation) | | |
|---|---|---|---|
| Cell-free system | MDL | WG | E. coli |
| SP6 transcript | | | |
| Prelysozyme | 5040 (1.0) | 3730 (1.0) | 0 (1.0) |
| omega prime prelysozyme | 5290 (1.0) | 10240 (2.8) | 1030 ( ) |
| Preprochymosin | 2470 (1.0) | 1110 (1.0) | 0 (1.0) |
| omega prime preprochymosin | 7280 (3.0) | 10010 (9.1) | 2180 ( ) |

In an analogous manner to the methods described above, various chimaeric RNA constructs were prepared with the NPT II coding region, and either omega prime, two tandem omega prime regions, a long (77 base) "junk" leader (polylinker) sequence or "junk" together with a central omega prime. The constructions are shown in FIG. 17 and the results in Table 8 below:

TABLE 8

EFFECT OF VARIOUS 5'-LEADER CONSTRUCTIONS ON IN VITRO TRANSLATION OF SP6 TRANSCRIPTS OF NEOMYCIN PHOSPHOTRANSFERASE

| | Cell-free Translation System | | | | | |
|---|---|---|---|---|---|---|
| | Wheat Germ | | Rabbit reticulocyte lysate | | E. coli | |
| | (−cap) | (+cap) | (−cap) | (+cap) | (−cap) | (+cap) |
| NPTII | 1* | 1 | 1 | 1 | 1 | 1 |
| omega prime NPTII | 8.1+ | 5.9 | 1.3 | 0.8 | 15.2 | 4.8 |
| [omega - omega] prime NPTII | 8.2 | 6.3 | 1.1 | 0.7 | 44.9 | 15.0 |
| "JUNK" - NPTII | 0.9 | 0.4 | 0.1 | 0.1 | 3.5 | 2.3 |
| "JUNK" - omega prime NPTII | 1.8 | 1.1 | 0.3 | 0.3 | 9.8 | 8.2 |

*Background (H$_2$O or linearized DNA) corrected/All values = Fold-stimulation over NPTII RNA alone.

This shows that a random polylinker sequence will not substitute for omega prime in 80S ribosome systems and only poorly in a prokaryotic (70S) system. Also two tandem omega primes only benefits 70S expression (c.f. single copy of omega prime).

To extend the data presented in Table 6 (above) on the effect of omega prime on expression of the β-glucuronidase mRNA (GUS mRNA), a new series of constructs utilized the GUS gene with a modified sequence context around the initiation codon (AUG). Plasmid pRAJ275, containing the "good context" leader

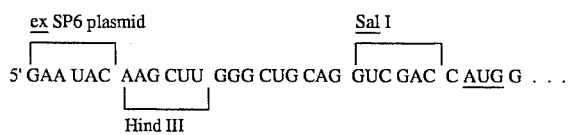

was the source for this version of GUS. Omega prime and various other leader constructs were inserted at the Hind III/Sal I sites as before. Details of the pRAJ275 construct areas follows:

pRAJ275 is a derivative of pRAJ255 (Jefferson, et al. Proc. Natl. Acad. Sci. 83, 8447 (1986)) in which the 5' sequences of GUS were removed by progressive BAL31 deletion and replaced with a synthetic oligonucleotide that has constructed a "consensus" translational initiator as defined by Kozak (Microbiol. Reviews, 47, 1 (1983)). This plasmid has a unique Nco I site (CCATGG) positioned at the initiator ATG codon, with the surrounding context GTC-GACCATGGTC. It has been shown both in vitro and in vivo that the context around the initiator can have a profound effect on the levels of translated product from a given amount of mRNA. This construction has been adjusted to maximise this effect. It was provided as a Sal I-Eco RI fragment in pUC19.

5'-capped or uncapped transcripts were electroporated into tobacco protoplasts as before and the level of GUS expression measured in extracts.

Uncapped RNAs were also added to MDL or WG cell-free translation systems and the level of GUS protein synthesized measured by excising and counting radioactive gel bands as for FIGS. 2, 3 etc. (Table 1). The results are shown in Table 9.

TABLE 9

Translational Enhancement by omega prime on GUS mRNA

| | | In vivo translation Electroporated tobacco protoplasts | | In vitro translation | | | |
|---|---|---|---|---|---|---|---|
| | | Gus activity nmoles 4-methyl umbelliferyl glucuronide cleaved min$^{-1}$/μg protein in protoplast extract | | MDL | | WG | |
| | Kozak context | | Fold stimulation | Cpm $^{35}$S methionine-labelled GUS in gel bands | Fold stimulation | Cpm $^{35}$S methionine-labelled GUS in gel bands | Fold stimulation |
| Uncapped RNAs | | | | | | | |
| GUS 235 (40b poly-linker leader) | bad | <0.01 | (1) | 7180 | (1.0) | 2400 | (1.0) |
| Omega prime - 235 | bad | 0.18 | (>18) | 19700 | (2.7) | 9720 | (4.1) |
| GUS 275 (28b poly-linker leader) | good | <0.01 | (1) | 12920 | (1.0) | 3010 | (1.0) |
| Omega prime - 275 | good | 0.35 | (>35) | 29280 | (2.3) | 19720 | (6.6) |
| 5' capped leader | | | | | | | |
| GUS 235 (40b poly-linker leader) | bad | 0.03 | (1) | | | | |
| Omega prime - 235 | bad | 0.61 | (20) | | | | |
| GUS 275 (28b poly-linker leader) | good | 0.04 | (1) | | | | |
| Omega prime - 275 | good | 3.2 | (80) | | | | |

Again in all cases, both in vitro (MDL, WG) and in vivo (protoplasts) with 5' capped or uncapped GUS mRNAs, with good or bad Kozak context around the initiation codon, omega prime enhances mRNA expression significantly.

A further set of RNA constructs was prepared, in an analogous manner to the method described above, with the E. coli reporter gene β-glucuronidase (GUS) and additionally the inducible trytophan (Trp) promoter. The Trp promoter was purchased from Pharmacia Ltd., and modified by conventional techniques of restriction endunuclease digestion, filling-in, sub-cloning etc, to create a 3'-Hind III site (FIG. 18) and a blunt 5'-end. This dsDNA fragment was then inserted into the various leader-reporter (GUS) gene plasmids between the SP6 promoter (silent in E. coli in vivo) and the 5'-leader construct of interest.

The resulting plasmid DNA was used to transform competent E. coli cells by standard techniques and the Trp promoter induced in situ to produce chimaeric leader-reporter mRNAs. Transcription start point corresponds to the G in the Hind III site (AAGCTT).

Expression of the transcripts in transformed E. coli cells was determined spectrophotometrically (Jefferson et al. Proc. Natl. Acad. Sci. 83 8447 (1986)). Results (Table 10) indicate that expression of GUS was enhanced in vivo from either the "good" or "bad" Kozak context construct by the presence of omega prime and to some extent by the other leader sequences or derivatives of omega prime.

TABLE 10

Expression controlled by the Trp promoter in stably transformed *E. coli* cells

| | Approximate relative spectro-photometric rates of conversion of p-nitrophenyl glucuronide |
|---|---|
| 235 - GUS ("Bad" context) | 1 |
| omega prime 235 GUS | 7× |
| 275 - GUS ("Good" context) | 1 |
| omega prime - 275 - GUS ("Good" context) | 8× |
| Δ1 - 275 - GUS | 5–8× |
| Δ2 275 GUS | (75×: To be confirmed) |
| Δ3 275 GUS | (75×: To be confirmed) |
| Δ4 275 GUS | 5–8× |
| Δ5 275 GUS | 5–8× |
| A → C 275 GUS | (75×: To be confirmed) |
| $[C,A]_n \to [U]_n$ 275 GUS | 5× |
| TYMV 275 GUS | 3–4× |
| A1MV4 275 GUS | 3–4× |
| BMV3 275 GUS | 1–2× |
| RSV 275 GUS | 1–2× |

(The results above were normalized to the respective GUS construct with the polylinker leader alone.

Conclusions

Omega prime enhances the expression of GUS RNA in vivo in *E. coli* transformed with plasmid DNAs, using Trp promoter in situ.

Further experiments were performed using supercoiled double stranded pUC19 DNA which is modified to contain the cauliflower mosaic virus (CaMV) 35S promoter, the nopaline synthase terminator (from *Agrobacterium tumefaciens*) and in between them either CAT DNA (●, ▲) or omega prime CAT DNA (O, Δ).

The constructs (FIG. 19) were prepared from a binary vector system (Bevan, Nuc Acids Res. 12 8711 (1984)) wherein the CaMV 35S promoter and the Nos terminator were excised using Hind III and Eco RI sites and inserted into plasmid pUC19 thus giving pUC35S Nos.

The constructs pUC35SCATNos and pUC35S omega prime CATNos were made by inserting either CAT or omega prime CAT respectively into the plasmids using the Bam HI site.

Various levels of either plasmid DNA (in μg/ml) were electroporated into protoplasts as before, and the cells incubated at 25° C. for 6 hours (O, ●) or 26 hours (Δ, ▲) and lysed. CAT assays (as before) were carried out.

Figure 20:
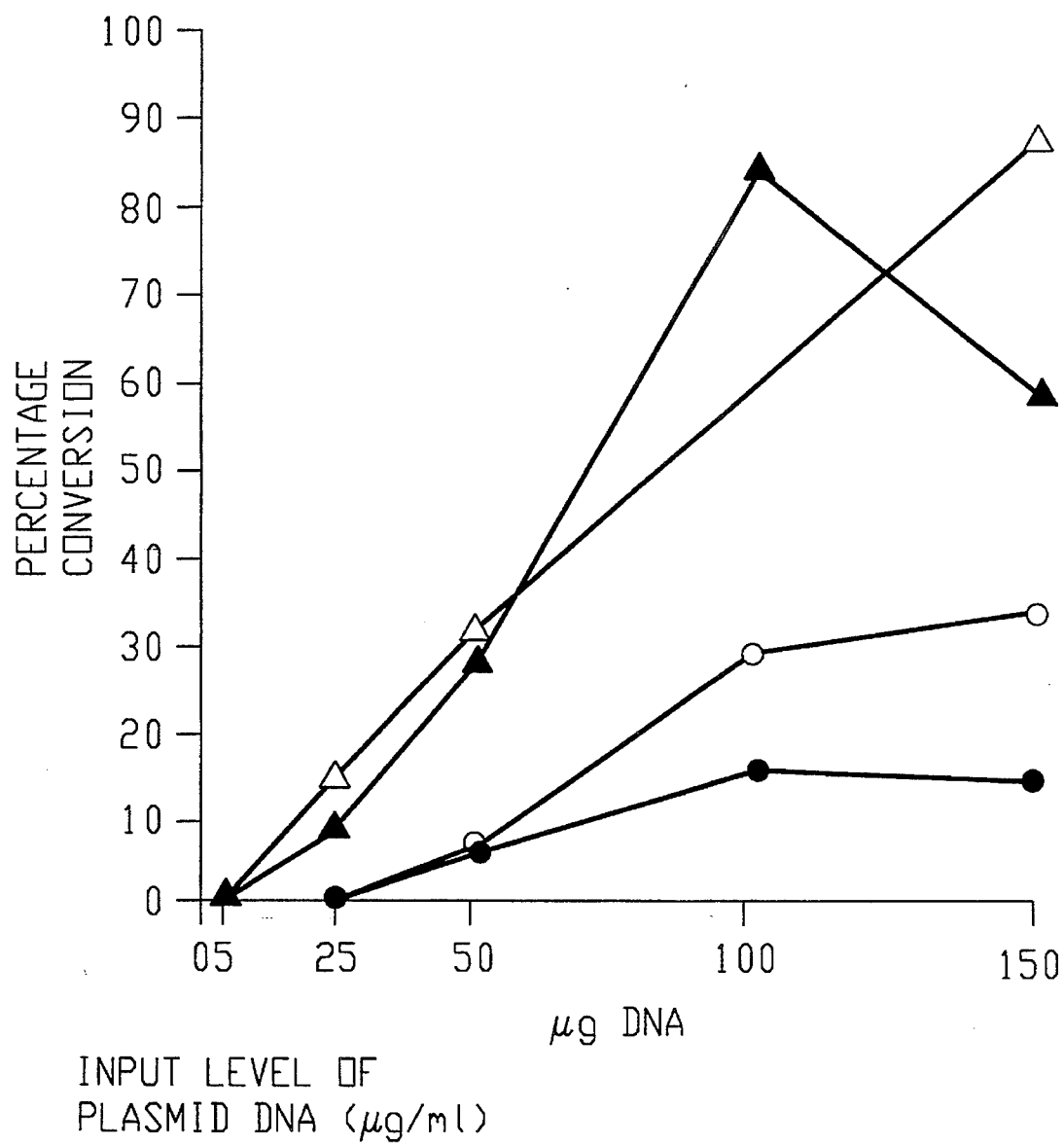
FIG. 20 Graph showing expression of CAT in constructs pUC35SCATNos and pUC35SΩ'CATNos.

The results as seen in FIG. 20 indicate that cells which received 100 μg–150 μg of supercoiled plasmid DNA showed enhanced CAT expression (2 fold) when omega prime is present in the construct (Δ, O).

These results show that gene expression in stable transgenic plants will also likely be enhanced by the inclusion of the omega prime sequence between the promoter (for transcription in vivo) and the translational open reading frame.

I claim:

1. DNA comprising two operatively linked subsequences, comprising:

i) a first subsequence comprised of a sequence complementary to the Ω' sequence of tobacco mosaic virus, and ii) a second subsequence downstream of said first subsequence and comprised of a coding sequence heterologous to said virus;

wherein, in mRNA produced by transcription of said first and second subsequences, mRNA complementary to said first subsequence is capable of enhancing translation of mRNA complementary to said second subsequence.

2. A cultured cell transformed with the DNA according to claim 1.

3. A cell line derived from a cell according to claim 2.

4. RNA comprising two operatively linked subsequences, comprising i) a first subsequence comprised of the Ω' sequence of tobacco mosaic virus, and ii) a second subsequence downstream of said first subsequence and comprised of a coding sequence heterologous to said virus;

wherein said first subsequence is capable of enhancing translation of said second sequence.

5. A DNA vector comprising:

i) a first subsequence comprised of a DNA sequence complementary to the Ω' sequence of tobacco mosaic virus, and ii) a second subsequence downstream of said first subsequence and comprised of a coding sequence heterologous to said virus;

wherein said first subsequence is capable of enhancing the translation of mRNA corresponding to said coding sequence heterologous to said virus.

* * * * *

UNITED STATES PATENT AND TRADEMARK OFFICE
CERTIFICATE OF CORRECTION

PATENT NO. : 5,489,527
DATED : February 6, 1996
INVENTOR(S) : Thomas M. A. WILSON It is certified that error appears in the above-indentified patent and that said Letters Patent is hereby corrected as shown below:

On the title page, Item [63], the Related U.S. Application Data is incorrect. It should read:

--[63] Related U.S. Application Data

Continuation of Ser. No. 148,650, filed Feb. 4, 1988, now abandoned, which was the National stage of International Application No. PCT/GB87/00390, on June 4, 1987.--

Signed and Sealed this

Sixth Day of August, 1996

*Attest:*

BRUCE LEHMAN

*Attesting Officer*     *Commissioner of Patents and Trademarks*